United States Patent
Swager et al.

(10) Patent No.: US 12,422,394 B2
(45) Date of Patent: Sep. 23, 2025

(54) DEVICES AND METHODS INCLUDING A PRECONCENTRATOR MATERIAL FOR DETECTION OF ANALYTES

(71) Applicant: Massachusetts Institute of Technology, Cambridge, MA (US)

(72) Inventors: Timothy Manning Swager, Newton, MA (US); Jisun Im, Busan (KR); Alexander Robertson Petty, Watertown, MA (US); Jan Markus Schnorr, Cambridge, MA (US); Cindy Schmädicke, Dresden (DE)

(73) Assignee: Massachusetts Institute of Technology, Cambridge, MA (US)

( * ) Notice: Subject to any disclaimer, the term of this patent is extended or adjusted under 35 U.S.C. 154(b) by 940 days.

(21) Appl. No.: 17/460,957

(22) Filed: Aug. 30, 2021

(65) Prior Publication Data

US 2022/0057352 A1 Feb. 24, 2022

Related U.S. Application Data

(62) Division of application No. 14/916,839, filed as application No. PCT/US2014/054405 on Sep. 5, 2014, now abandoned.

(Continued)

(51) Int. Cl.
*B01L 3/00* (2006.01)
*B01F 33/302* (2022.01)
(Continued)

(52) U.S. Cl.
CPC ............ *G01N 27/127* (2013.01); *B82Y 15/00* (2013.01); *G01N 1/405* (2013.01); *G01N 27/04* (2013.01);
(Continued)

(58) Field of Classification Search
CPC ...... G01N 27/127; G01N 1/405; G01N 27/04; G01N 33/0013; G01N 33/0047; G01N 33/0019; B82Y 15/00
See application file for complete search history.

(56) References Cited

U.S. PATENT DOCUMENTS

| | | |
|---|---|---|
| 6,119,699 A | 9/2000 | Sung |
| 6,171,378 B1 | 1/2001 | Manginell et al. |

(Continued)

FOREIGN PATENT DOCUMENTS

| | | |
|---|---|---|
| CN | 101664228 A | 3/2010 |
| GB | 863394 A | 3/1961 |

(Continued)

OTHER PUBLICATIONS

PCT/US2015/054405, Dec. 3, 2014, International Search Report and Written Opinion.

(Continued)

*Primary Examiner* — Jennifer Wecker
*Assistant Examiner* — Oyeleye Alexander Alabi
(74) *Attorney, Agent, or Firm* — Wolf, Greenfield & Sacks, P.C.

(57) ABSTRACT

Embodiments described herein provide devices and methods for the determination of analytes. The device typically includes an absorbent material that allows for an analyte sample to be concentrated and analyzed simultaneously and within a short period of time (e.g., less than 10 seconds). Embodiments described herein can provide portable and easily operable devices for on-site, real time field monitoring with high sensitivity, selectivity, and fast response time.

21 Claims, 23 Drawing Sheets

Related U.S. Application Data

(60) Provisional application No. 62/024,300, filed on Jul. 14, 2014, provisional application No. 61/990,293, filed on May 8, 2014, provisional application No. 61/874,650, filed on Sep. 6, 2013.

(51) Int. Cl.

| | | |
|---|---|---|
| *B01F 33/3033* | (2022.01) | |
| *B01L 7/00* | (2006.01) | |
| *B01L 9/00* | (2006.01) | |
| *B23D 63/00* | (2006.01) | |
| *B29C 37/00* | (2006.01) | |
| *B65G 47/80* | (2006.01) | |
| *B82Y 15/00* | (2011.01) | |
| *B82Y 20/00* | (2011.01) | |
| *B82Y 30/00* | (2011.01) | |
| *B82Y 40/00* | (2011.01) | |
| *C12M 1/34* | (2006.01) | |
| *C12M 3/06* | (2006.01) | |
| *C12N 1/14* | (2006.01) | |
| *C12N 1/20* | (2006.01) | |
| *C12Q 1/02* | (2006.01) | |
| *C12Q 1/6806* | (2018.01) | |
| *C12Q 1/6844* | (2018.01) | |
| *C12Q 1/6848* | (2018.01) | |
| *C12Q 1/686* | (2018.01) | |
| *C23C 2/00* | (2006.01) | |
| *G01N 1/40* | (2006.01) | |
| *G01N 15/10* | (2024.01) | |
| *G01N 15/14* | (2024.01) | |
| *G01N 15/1433* | (2024.01) | |
| *G01N 21/29* | (2006.01) | |
| *G01N 21/41* | (2006.01) | |
| *G01N 21/45* | (2006.01) | |
| *G01N 21/65* | (2006.01) | |
| *G01N 27/04* | (2006.01) | |
| *G01N 27/12* | (2006.01) | |
| *G01N 33/00* | (2006.01) | |
| *G01N 33/543* | (2006.01) | |
| *G01N 33/574* | (2006.01) | |
| *G01N 33/58* | (2006.01) | |
| *G02B 6/42* | (2006.01) | |

(52) U.S. Cl.
CPC ..... *G01N 33/0013* (2013.01); *G01N 33/0047* (2013.01); *G01N 33/0019* (2024.05)

(56) References Cited

U.S. PATENT DOCUMENTS

| | | | | |
|---|---|---|---|---|
| 6,902,701 | B1* | 6/2005 | Hughes | G01N 1/405 |
| | | | | 422/50 |
| 11,109,619 | B2 | 9/2021 | Swager et al. | |
| 2003/0000538 | A1* | 1/2003 | Bereman | A24B 15/246 |
| | | | | 131/310 |
| 2006/0249382 | A1 | 11/2006 | Hengstenberg et al. | |
| 2008/0248578 | A1* | 10/2008 | Deans | G01N 21/643 |
| | | | | 422/68.1 |
| 2009/0293590 | A1 | 12/2009 | Zeng et al. | |
| 2010/0063225 | A1 | 3/2010 | Swager et al. | |
| 2011/0081724 | A1* | 4/2011 | Swager | B82Y 15/00 |
| | | | | 977/773 |
| 2011/0089051 | A1* | 4/2011 | Wang | B82Y 40/00 |
| | | | | 977/788 |
| 2011/0159160 | A1 | 6/2011 | Jonsson et al. | |
| 2012/0037306 | A1 | 2/2012 | Dai et al. | |
| 2012/0116094 | A1 | 5/2012 | Swager et al. | |
| 2012/0125547 | A1* | 5/2012 | Akai | C08J 5/005 |
| | | | | 428/401 |
| 2012/0220053 | A1 | 8/2012 | Lee et al. | |
| 2013/0113359 | A1 | 5/2013 | Swager et al. | |
| 2013/0220349 | A1 | 8/2013 | Robertson et al. | |
| 2013/0273665 | A1 | 10/2013 | Swager et al. | |
| 2014/0346042 | A1 | 11/2014 | Shimoyama et al. | |
| 2015/0323482 | A1 | 11/2015 | Shimoyama et al. | |
| 2016/0231267 | A1 | 6/2016 | Swager et al. | |
| 2016/0192701 | A1 | 7/2016 | Swager et al. | |

FOREIGN PATENT DOCUMENTS

| | | |
|---|---|---|
| JP | 2001-526059 A | 12/2001 |
| JP | 2004-500901 A | 1/2004 |
| JP | 2011-526202 A | 10/2011 |
| WO | 99/32002 A1 | 7/1999 |
| WO | 02/00046 A1 | 1/2002 |
| WO | WO 2008/133779 A2 | 11/2008 |
| WO | WO 2009/136978 A2 | 11/2009 |
| WO | WO 2009/156763 A1 | 12/2009 |
| WO | WO 2010/123482 A2 | 10/2010 |
| WO | WO 2011/044221 A2 | 4/2011 |
| WO | WO 2011/056936 A2 | 5/2011 |
| WO | WO 2012/044778 A1 | 4/2012 |
| WO | WO 2012/067665 A1 | 5/2012 |

OTHER PUBLICATIONS

PCT/US2014/054405, Mar. 17, 2016, International Preliminary Report on Patentability.

PCT/US2014/054391, Dec. 4, 2014, International Search Report and Written Opinion.

PCT/US2014/054391, Mar. 17, 2016, International Preliminary Report on Patentability.

International Search Report and Written Opinion for PCT/US2014/054405 mailed Dec. 3, 2014.

International Preliminary Report on Patentability for PCT/US2014/054405 mailed Mar. 17, 2016.

International Search Report and Written Opinion for PCT/US2014/054391, mailed Dec. 4, 2014.

International Preliminary Report on Patentability for PCT/US2014/054391, mailed Mar. 17, 2016.

Alam et al., Development of polyaniline-modified polysulfone nanocomposite membrane. Appl Water Sci. Nov. 29, 2011;2:37-46. Epub 2012.

Esser et al., Selective detection of ethylene gas using carbon nanotube-based devices: utility in determination of fruit ripeness. Angew Chem Int Ed Engl. Jun. 4, 2012;51(23):5752-6. doi: 10.1002/anie.201201042. Epub Apr. 19, 2012.

Girschikofsky et al., Optical planar Bragg grating sensor for real-time detection of benzene, toluene and xylene in solvent vapour. Sensors and Actuators B: Chemical. Sep. 30, 2012;171:338 42.

Hrapovic et al., Metallic nanoparticle-carbon nanotube composites for electrochemical determination of explosive nitroaromatic compounds. Anal Chem. Aug. 1, 2006;78(15):5504-12.

Im et al., Integrated Gas Sensing System of SWCNT and Cellulose Polymer Concentrator for Benzene, Toluene, and Xylenes. Sensors (Basel). Feb. 2, 2016;16(2):183. doi: 10.3390/s16020183.

Kadir et al., Optical waveguide BTX gas sensor based on polyacrylate resin thin film. Environ Sci Technol. Jul. 1, 2009;43(13):5113-6.

Kim et al., Analytical bias among different gas chromatographic approaches using standard BTX gases and exhaust samples. J Sep Sci. Feb. 2009;32(4):549-58. doi: 10.1002/jssc.200800556.

Li et al., Carbon Nanotube Sensors for Gas and Organic Vapor Detection. Nano Letters. Jun. 13, 2003;3(7):929-33. doi: 10.1021/nl034220x.

Lobez et al., Radiation detection: resistivity responses in functional poly(olefin sulfone)/carbon nanotube composites. Angew Chem Int Ed Engl. 2010;49(1):95-8. doi: 10.1002/anie.200904936.

Meadows et al., Alkali metal cation-pi interactions observed by using a lariat ether model system. J Am Chem Soc. Apr. 4, 2001;123(13):3092-107.

(56) References Cited

OTHER PUBLICATIONS

Parsons et al., Real-time monitoring of benzene, toluene, and p-xylene in a photoreaction chamber with a tunable mid-infrared laser and ultraviolet differential optical absorption spectroscopy. Appl Opt. Feb. 1, 2011;50(4):A90-9. doi: 10.1364/AO.50.000A90.
Qi et al., Toward Large Arrays of Multiplex Functionalized Carbon Nanotube Sensors for Highly Sensitive and Selective Molecular Detection. Nano Letters. Mar. 1, 2003;3(3):347-51. Epub Feb. 6, 2003.
Shey et al., The azidation of starch. Carbohydrate polymers, 65(4), 529-534. doi:10.1016/j.carbpol.2006.02.009.
Tumbiolo et al., Determination of benzene, toluene, ethylbenzene and xylenes in air by solid phase micro-extraction/gas chromatography/mass spectrometry. Anal Bioanal Chem. Nov. 2004;380(5-6):824-30.
Tunckol et al., Carbon nanomaterial-ionic liquid hybrids. Carbon. 2012;50(4):4303-34.
Wang et al., Carbon Nanotube/Polythiophene Chemiresistive Sensors for Chemical Warfare Agents. J Am Chem Soc. Apr. 23, 2008;130(16):5392-3. doi: 10.1021/ja710795k. Epub Mar. 29, 2008.
Young et al., Infrared hollow waveguide sensors for simultaneous gas phase detection of benzene, toluene, and xylenes in field environments. Anal Chem. Aug. 15, 2011;83(16):6141-7. doi: 10.1021/ac1031034. Epub Jun. 29, 2011. Erratum in: Anal Chem. Aug. 15, 2011;83(16):6147.
Zhang et al., Functionalization of single-walled carbon nanotubes and fullerenes via a dimethyl acetylenedicarboxylate-4-dimethylaminopyridine zwitterion approach. J Am Chem Soc. Jun. 27, 2007;129(25):7714-5. Epub Jun. 2, 2007.

\* cited by examiner

|  | FSPh-CA | Ph-CA | Py-CA | Benz-CA | Calix-CA |
|---|---|---|---|---|---|
| DS | 0.8 | 0.59 | 0.46 | 0.42 | 0.5 |
| Mn (Da) | 85 K | 58 K | 65 K | 58 K | 89 K |
| PDI | 1.77 | 1.76 | 2.13 | 2.85 | 3.35 |

Route 1. Copper(I)-Catalyzed Azide-Alkyne Cycloaddition (CuACC) Reaction

Step 1. One pot azidation

Step 2. Copper(I)-catalyzed azide-alkyne cycloaddition

Route 2. Esterification Reaction

R = H or an organic side chain
R' = H or an organic group
Y = O, S, NR, CR=CR
n = greater than 1

R = H or an organic side chain
R' = H or an organic group
n = greater than 1

1

P3

P4

P5

DEVICES AND METHODS INCLUDING A PRECONCENTRATOR MATERIAL FOR DETECTION OF ANALYTES

RELATED APPLICATIONS

This application is a Division of U.S. application Ser. No. 14/916,839, filed Jun. 30, 2016, entitled "DEVICES AND METHODS INCLUDING A PRECONCENTRATOR MATERIAL FOR DETECTION OF ANALYTES", which is a national stage filing under 35 U.S.C. § 371 of International Patent Application Serial No. PCT/US2014/054405, filed Sep. 5, 2014, entitled "DEVICES AND METHODS INCLUDING A PRECONCENTRATOR MATERIAL FOR DETECTION OF ANALYTES", which claims priority under 35 U.S.C. § 119(e) to U.S. Provisional Application Ser. No. 62/024,300, filed on Jul. 14, 2014, entitled "DEVICES AND METHODS INCLUDING A PRECONCENTRATOR MATERIAL FOR DETECTION OF ANALYTES", and to U.S. Provisional Application Ser. No. 61/990,293, filed on May 8, 2014, entitled "DEVICES AND METHODS INCLUDING A PRECONCENTRATOR MATERIAL FOR DETECTION OF ANALYTES", and to U.S. Provisional Application Ser. No. 61/874,650, filed Sep. 6, 2013, entitled "DEVICES AND METHODS INCLUDING A PRECONCENTRATOR MATERIAL FOR DETECTION OF ANALYTES", the contents of each of which is incorporated herein by reference in its entirety for all purposes.

FIELD

Embodiments described herein relate to devices comprising absorbent materials for the determination of analytes, and related methods.

BACKGROUND

Chemical sensing technologies have focused on the detection of hydrocarbon analytes. For example, benzene, toluene, and xylenes (BTX) are important chemicals as starting and intermediate materials for a wide range of products and are produced largely from petroleum, e.g., pyrolysis gasoline and reformate. BTX are, however, known to be toxic and benzene is classified as a carcinogen. Therefore, facile methods to monitor BTX in chemical and petrochemical industries and refineries can be essential for the safety of work places and the environment as well as process and quality control of products. The permissible exposure limits (PELs) as 8-hour time-weighted average (TWA) concentrations by the Occupational Safety and Health Administration (OSHA) for benzene, toluene, and xylenes are 1 ppm (5 ppm as a short-term exposure limit (STEL)), 200 ppm (500 ppm as STEL), and 100 ppm (150 ppm as STEL), respectively.

Another important analyte in chemical sensing is the fruit hormone ethylene. Fruit emits ethylene during its ripening process and ethylene gas in its vicinity can lead to accelerated ripening. Measuring ethylene at relevant levels for the food industry therefore allows an estimate of fruit ripeness and ethylene sensors can be utilized to guide decisions that lead to a reduction in waste and spoilage of produce in agriculture, storage, transportation, and distribution.

Many of the available monitoring systems for hydrocarbons such as BTX or ethylene involve gas chromatography (GC) coupled with mass spectrometer (MS) and flame ionization detection (FID). The detection limit of GC/MS or GC/FID techniques can be as low as parts-per-billion (ppb), but there are limitations for real time, on-site analysis of hydrocarbon traces due to relatively long sampling, preconcentrating, and transferring steps prior to detection. Furthermore, special operation and analysis expertise are required for the detection.

Optical sensors based on infrared and ultraviolet spectroscopies and optical wave guides for on-site field analyte gas detection have exhibited sub-parts-per-million (ppm) detection limits. In most cases, a preconcentration step prior to sensing is necessary to detect sub-ppm level of the gases. For example, a preconcentrator consisting of polymeric or carbon-based absorbents collects analytes, and the concentrated analytes are then delivered to a sensing unit by thermal desorption. The preconcentration step typically takes from tens of minutes to several hours, and a thermal desorption system requires high power consumption, rendering such as a system challenging for portable and on-site field sensing applications.

SUMMARY

Devices, systems, and methods for determining an analyte are disclosed.

In some embodiments, the device comprises a sensor material layer comprising a conductive material; and an absorbent material layer disposed on the sensor material layer, wherein the absorbent material interacts with an analyte, if present, in a manner bringing the analyte into proximity with the sensor material to produce a determinable signal from the device.

In some embodiments, the device comprises a first electrode and a second electrode; a sensor material in electrochemical communication with the first and the second electrodes, wherein resistance to current flow between the first and second electrode is affected by the sensor material; and an absorbent material in contact with the sensor material, wherein the absorbent material interacts with the analyte, if present, in a manner bringing the analyte into sufficient proximity with the sensor material such that resistance to current flow between the first and second electrodes is affected, thereby generating a signal in the device by which the analyte is determined.

In some embodiments, methods are provided comprising exposing a sample suspected of containing an analyte to a device comprising a sensor material and an absorbent material in contact with the sensor material, the absorbent material having a first analyte concentration prior to exposure to the sample and a second analyte concentration upon exposure to the sample, wherein the sensor material produces a determinable signal affected by the analyte concentration of the absorbent material; and determining the determinable signal of the sensor material, thereby determining the analyte.

In some embodiments, methods are provided comprising exposing a sample suspected of containing an analyte to a device comprising a first electrode, a second electrode, a sensor material in electrical communication with the first and second electrodes, and an absorbent material in contact with the sensor material, wherein the analyte, if present, interacts with the sensor material to cause a change in resistance between the first and second electrodes; and determining the change in resistance between the first and second electrodes, thereby determining the analyte.

BRIEF DESCRIPTION OF THE DRAWINGS

(FIG. 1B) functionalized cellulose acetates that can be used as preconcentrators (DS: degree of substitution, $M_n$: number average molecular weight, and PDI: polydispersity index); and (FIG. 1C) a schematic diagram for functionalization of cellulose acetate and its use in sensing applications.

(FIG. 2A) and (FIG. 2C) frequency changes upon exposure to benzene and toluene, respectively; (FIG. 2B) and (FIG. 2D) mass uptakes upon exposure to benzene and toluene, respectively.

Figure 1A:
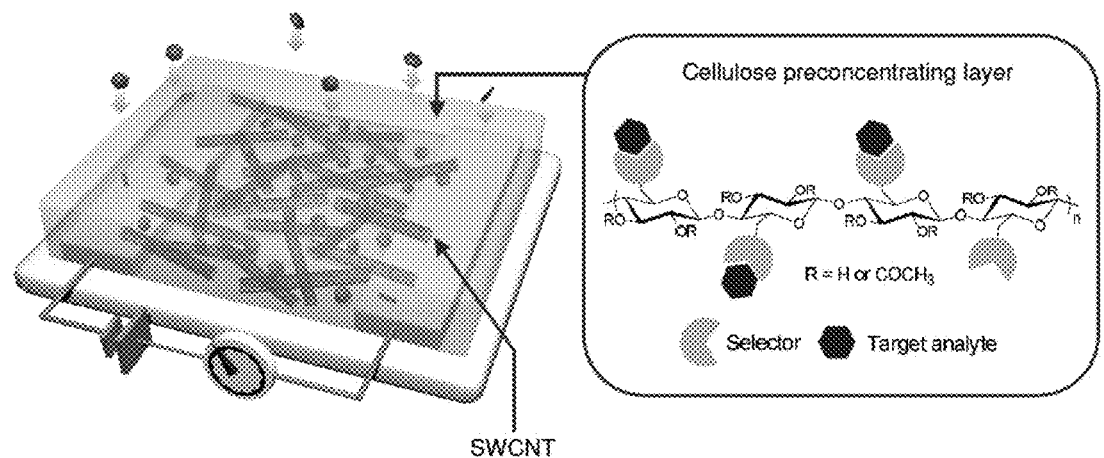
FIGS. 1A-1C shows (FIG. 1A) a schematic diagram of a device including an absorbent layer disposed on a sensor material layer, where absorbent layer absorbs, concentrates, and delivers analytes as near as possible to the sensor material layer within a few seconds.

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

Embodiments described herein provide devices and methods for the determination of analytes. In some cases, the device includes a material capable of producing a concentrated sample of a target analyte, for example, from a vapor sample, and/or delivering an analyte sample to a sensing component of the device. In some embodiments, the analyte sample may be concentrated and analyzed simultaneously and within a short period of time (e.g., less than 10 seconds). This may be advantageous in that a separate analyte preconcentration process, involving concentrating an analyte in a preconcentration material and then removing the concentrated analyte from the preconcentration material for delivery to an external sensor, may not be necessary. Additionally, devices may be configured such that unwanted phase separation between components of the device is reduced or eliminated. Embodiments described herein can provide portable and easily operable devices for on-site, real time field monitoring with high sensitivity, selectivity, and fast response time.

In some embodiments, devices for determining analytes are provided. Typically, the device may include a first electrode, a second electrode, and a sensor material arranged in electrochemical communication with the first and the second electrodes. The sensor material may include a conductive material (e.g., a carbon-based nanostructure), such that resistance to current flow between the first and second electrode is affected by interaction of the sensor material. Upon exposure to an analyte, the analyte may interact with the sensor material to affect resistance to current flow between the first and second electrodes, thereby generating a signal in the device by which the analyte is determined. In some embodiments, the sensor material is in substantially solid form.

Some embodiments involve the use of an absorbent material in combination with (e.g., in contact with) the sensor material. In some embodiments, the absorbent material may be in substantially solid form. For example, the absorbent material may be formed as a layer, coating, powder, fiber or network of fibers, or other solid articles. In some cases, the absorbent material is a polymeric material such as a cellulose-based polymer, a fluorinated polymer, or a substantially hydrophobic polymer. In some embodiments, the absorbent material comprises an ionic liquid. The absorbent material may be capable of interacting with the analyte, such that the analyte intercalates or diffuses into the absorbent material, creating a concentrated sample of the analyte. That is, the absorbent material can be useful as "preconcentrator" for analytes. The analyte may be readily determined upon intercalation of the analyte within the absorbent material layer. In some cases, the analyte may be determined without removal of the analyte from the absorbent material layer. In some embodiments, the absorbent material may include moieties that bind or otherwise associate with analytes of interest, as described more fully below. Such materials may be useful in the detection of analytes at low concentrations (e.g., low ppm) including vapor-phase analytes. The absorbent material may also interact with an analyte in a manner bringing the analyte into proximity with the sensor material to produce a determinable signal from the device. For example, the absorbent material may "deliver" an analyte sample at or near the interface between the absorbent material and the sensor material, enhancing the sensitivity of the device.

The absorbent material may also improve device performance by, for example, enhancing sensitivity, selectivity, stability, and/or lifetime of the device. For example, the absorbent material may improve the selectivity of the device by reducing or preventing contact between the sensor material and contaminants or other undesired species (e.g., polar interferents such as water). The absorbent material may also improve sensitivity of the device by interacting with the desired analyte and thus increasing the local concentration of the analyte in the vicinity of the sensor material. In some cases, the absorbent material may serve as a moisture barrier, reducing or eliminating undesired and/or irreversible interactions between the sensor material and water. The absorbent material may also provide mechanical stability to the device, and in the case that it has a high glass transition temperature, can prevent movement of the sensor material caused, for example, by exposure to solvents or by changes in temperature.

In some embodiments, the absorbent material and sensor material may be arranged in a layered structure within the device. For example, the device may include a sensor material layer with an absorbent material layer (e.g., substituted cellulose) disposed on the sensor material layer. In some cases, the absorbent material layer may form a coating on at least a portion of the sensor material layer. In some cases, the absorbent material layer may form a coating on substantially all of the sensor material layer. For example, the absorbent material layer may form a coating that encapsulates the sensor material layer and optionally the electrodes contacting the sensor material layer. FIG. 1A shows an embodiment where an absorbent material layer including functionalized cellulose can be formed on a sensor material layer comprising single-walled carbon nanotubes, such that analytes can diffuse through absorbent material layer and can be delivered as near as possible to the sensor material layer, which enhances the sensitivity of the system. Such an arrangement can provide the ability to both (1) preconcentrate an analyte sample and (2) determine the analyte simultaneously and/or rapidly. In some cases, analyte preconcentration and analyte determination may be performed within a few seconds of initial contact with the sample (e.g., vapor sample) suspected of containing the analyte, allowing for on-site, real-time determination of analytes.

The absorbent material may include one or more binding sites that selectively interact with one or more analytes, and/or may be responsive to a change in a set of conditions in the surrounding environment (e.g., temperature, pH, etc.). The binding site may incorporated within the absorbent material in various configurations. For example, the binding site may be a small molecule, a polymer, a biological binding site, or the like. In some embodiments, the binding site may comprise ionic binding site (e.g., a salt). In some embodiments, the binding site may comprise a neutral binding site. The binding site may be an organic, organometallic, or an inorganic binding site. In some cases, the binding site may be attached to the absorbent material via a covalent bond. In some cases, the binding site may be substantially contained within (e.g., dispersed within) the absorbent material, and may not form a covalent bond to the absorbent material. In some embodiments, the absorbent material layer may include a polymer material and a plurality of binding sites. The plurality of binding sites may be covalently or non-covalently bonded to the polymer material. In some cases, the plurality of binding sites may be dispersed throughout the polymer material.

The interaction between the analyte and the binding site may comprise formation of a bond, such as a covalent bond (e.g. carbon-carbon, carbon-oxygen, oxygen-silicon, sulfur-sulfur, phosphorus-nitrogen, carbon-nitrogen, metal-oxygen or other covalent bonds), an ionic bond, a hydrogen bond (e.g., between hydroxyl, amine, carboxyl, thiol and/or similar functional groups, for example), a dative bond (e.g. complexation or chelation between metal ions and monodentate or multidentate ligands), and the like. The interaction may also comprise Van der Waals interactions. In one embodiment, the interaction comprises forming a covalent bond with an analyte. In some cases, the interaction between the binding site and the analyte may comprise a reaction, such as a charge transfer reaction. In other embodiments, the binding site and/or another device component may undergo a chemical or physical transformation upon a change in the surrounding environment (e.g., change in temperature) to produce a determinable signal from the device.

In some cases, the binding site may comprise a biological or a chemical group capable of binding another biological or chemical molecule in a medium (e.g., solution, vapor phase, solid phase). For example, the binding site may include a functional group, such as a thiol, aldehyde, ester, carboxylic acid, hydroxyl, and the like, wherein the functional group forms a bond with the analyte. In some cases, the binding site may be an electron-rich or electron-poor moiety wherein interaction between the analyte and the binding site comprises an electrostatic interaction. In some cases, the interaction between the analyte and the binding site includes binding to a metal or metal-containing moiety. The binding site may also interact with an analyte via a binding event between pairs of biological molecules including proteins, nucleic acids, glycoproteins, carbohydrates, hormones, and the like.

In some embodiments, the binding site may contain an aromatic species, including monocyclic aromatic groups (e.g., phenyl groups) or polycyclic aromatic hydrocarbons (e.g., naphthalene, phenanthrene, pyrene, anthracene, fluoranthene, perylene, benzopyrene, etc.), any of which are optionally substituted. In some cases, the aromatic species may be substituted with one or more halo-containing groups. In one set of embodiments, the binding site is a fluorine-containing aromatic species. For example, the binding site may be an aromatic species substituted with one or more fluoro-groups, or one or more fluoroalkyl groups (e.g., —$CF_3$). As an illustrative embodiment, the binding site may include an electron-deficient aromatic group, such as a pentafluorophenyl group, which may be useful in the determination of electron-rich aromatic analytes, such as benzene, toluene, xylene, and benzopyrene (e.g., benzo[a]pyrene).

In some embodiments, the binding site may be a metal-containing binding site. For example, the binding site may include metal salts or metal complexes (e.g., organometallic complexes). In some embodiments, the metal salt is a transition metal salt. In some cases, the binding site may include a metal complex or metal salt comprising Cu(I), Cu(II), Ag(I), Ag(II), Co(II), Co(III), Rh(I), Rh(III), Ir(I), Ir(III) or Pd(II). Some examples of metal salts or metal complexes include, but are not limited to, $TiO_2$, $TiCl_4$, and other titanium salts, AgCl, $AgPF_6$, $Ag(OCOCF_3)$, $Ag(SO_3CF_3)$, and other silver salts, $PtCl_2$ and other platinum salts, $Au_2Cl_6$ and other gold salts, $Al(OEt)_3$ and other aluminum salts, $Ni(SO_3CF_3)_2$, $NiCl_2$, and other nickel salts, and $Cu(SO_3CF_3)$ and other copper salts. In some cases, the binding site may be a copper-containing binding site. In some cases, the copper-containing binding site is a salt, such as a Cu(II) salt. In some cases, the binding site may be a cobalt-containing binding site. In some cases, the cobalt-containing binding site is a salt, such as a Co(II) or Co(III) salt (e.g., a cobalt (III) porphyrin compound). In some cases, the binding site may be a palladium-containing binding site. In some cases, the palladium-containing binding site is a salt, such as a Pd(II) salt. Some examples of specific metal containing binding site include, but are not limited to,

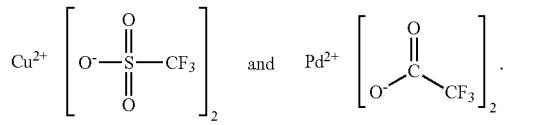

In some embodiments, the binding site may be a metal complex capable of interacting with ethylene. An example of such a metal complex is described in Esser et al., "Selective Detection of Ethylene Gas Using Carbon Nanotube-based Devices: Utility in Determination of Fruit Ripeness," Angew. Chem. Int. Ed. 2012, 51(23), 5752-5756, the contents of which are incorporated herein by reference in its entirety for all purposes.

In some embodiments, the binding site may be a quinone-containing binding site or an oxidized derivative of an aromatic group, including polycyclic aromatic groups. Examples of such binding site include 1,4-benzoquinones or cyclohexadienediones, 1,2-benzoquinones (ortho-quinones), 1,4-naphthoquinones and 9,10-anthraquinones. And the like. In one embodiment, the binding site is 2,3-dichloro-5,6-dicyano-1,4-benzoquinone (DDQ).

In some cases, the binding site may include a calixarene group. The calixarene group may include a plurality of aromatic rings (e.g., phenyl rings). In some embodiments, the calixarene includes 4 to 12 aromatic rings.

In some cases, the binding site may include a iptycene group (e.g., triptycene, pentiptycene, etc.).

In some cases, the binding site may include a hydrogen-bond donor. In some cases, the binding site may include a hydrogen bond acceptor. Those of ordinary skill in the art would be able to identify hydrogen-bond donors or hydrogen-bond acceptors suitable for use in embodiments described herein. For example, a hydrogen-bond donor may comprise at least one hydrogen atom capable of interacting with a pair of electrons on a hydrogen-bond acceptor to form the hydrogen bond. In some cases, the hydrogen atom may be positioned adjacent to an electron-poor group, such as fluorine, nitro, acyl, cyano, sulfonate, or the like, to increase the acidity of the hydrogen atom and, thus, the ability of the hydrogen atom to form a hydrogen bond. Other examples of groups which may form hydrogen bonds include carbonyl groups, amines, hydroxyls, and the like. In one embodiment, the hydrogen-bond donor is a fluorinated alcohol, such as hexafluoroisopropanol. In some embodiments, the hydrogen-bond acceptor may be a carbonyl group, an amine, an imine, or other groups containing a pair of electrons that can interact with a hydrogen atom on another species via hydrogen bonding.

Some specific examples of binding sites include the following groups:

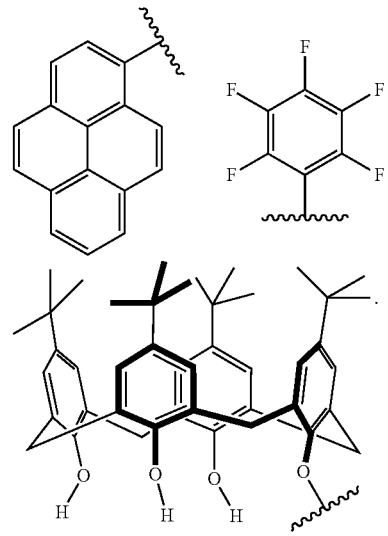

Some embodiments involve the use of an absorbent material. The absorbent material may be selected, and may be appropriately functionalized, to impart desired characteristics (e.g., surface properties) to the device. In some cases, the absorbent material may include functional groups selected to facilitate absorption of an analyte, and/or to minimize or prevent absorption of undesired species (e.g., contaminants). For example, the absorbent material may be selected to have a particular surface area or surface property (e.g., hydrophobicity, hydrophilicity, electrostatic charge, etc.). In some cases, the absorbent material may be selected to be compatible with other components of the device, such as the sensor material. For example, the absorbent material may be selected to promote adhesion and reduce or prevent separation/delamination of components (e.g., layers) within the device at various temperatures.

In some cases, the absorbent material may include a conjugated polymer (e.g., pi-conjugated, sigma-conjugated), or a non-conjugated polymer (e.g., cellulose-based polymer). In some cases, the absorbent material may include primarily non-polar groups. In some cases, the absorbent material absorbent material may include a substantially hydrophobic polymer. For example, incorporation of a substantially hydrophobic polymer within a device as described herein may minimize or prevent entry of water within at least a portion of the device. In some cases, the absorbent material absorbent material may include a substantially hydrophilic polymer. In some cases, the absorbent material may be the polymer may be a fluorinated polymer. In some embodiments, the absorbent material layer includes a polyvinyl alcohol-based material. In some embodiments, the absorbent material layer includes a polyhydroxyl ethyl methacrylate-based material. In some cases, the polymer may include one or more iptycene-based groups (e.g., triptycenes, pentiptycenes, etc.). In each of these cases, the polymer may be appropriately functionalized to be responsive to a particular analyte or set of analytes.

In some embodiments, the absorbent material layer may include a cellulose-based polymer. For example, the cellulose-based polymer can be cellulose, cellulose acetate, cellulose diacetate, or cellulose triacetate, any of which is optionally substituted. In some embodiments, the cellulose-based polymer is cellulose substituted with at least one binding site. For example, the cellulose-based polymer may include a functional group that contains an aromatic moiety (e.g., an electron deficient aromatic moiety) that is capable of binding an aromatic species. The aromatic moiety may be, for example, an optionally substituted monocyclic aromatic group (e.g., phenyl group) or an optionally substituted polycyclic aromatic hydrocarbon. In some cases, the cellulose-based polymer is functionalized with a calixarene group. In cases where the target analyte is an electron rich species (e.g., benzene, toluene, xylene, benzo[a]pyrene), the aromatic moiety may be substituted with electron deficient groups, such as fluoro groups, to enhance interaction with the target analyte.

In one set of embodiments, the cellulose-based polymer contains the structure,

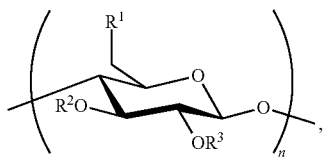

wherein:
R$^1$ is a group comprising a binding site for an aromatic species;
R$^2$ and R$^3$ can be the same or different and are hydrogen, alkyl, aryl, a carbonyl group, any of which is optionally substituted; and
n is greater than 1.

In some cases, R$^2$ and R$^3$ can be the same or different and are hydrogen, —COCH$^3$, or —F$^5$Ph. In some cases, R$^2$ and R$^3$ are the same. In some cases, R$^2$ and R$^3$ are different.

In another set of embodiments, the cellulose-based polymer contains the structure,

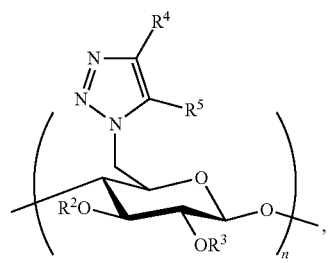

wherein R$^4$ and R$^5$ can be the same or different and are hydrogen, alkyl, alkenyl, aryl, heteroalkyl, heteroalkenyl, heteroaryl, or carbonyl group, any of which is optionally substituted.

In another set of embodiments, the cellulose-based polymer contains the structure,

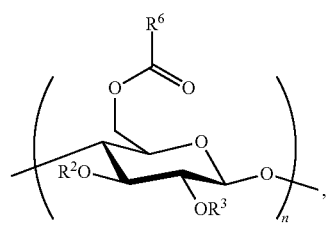

wherein R$^6$ is alkyl, alkenyl, aryl, heteroalkyl, heteroalkenyl, or heteroaryl, any of which is optionally substituted.

In some cases, the cellulose-based polymer may include one of the following groups,

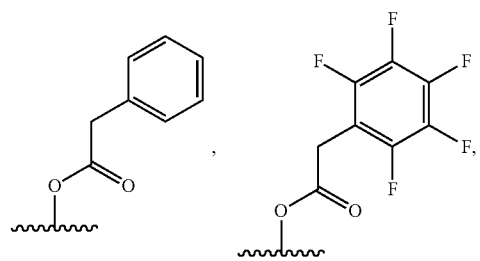

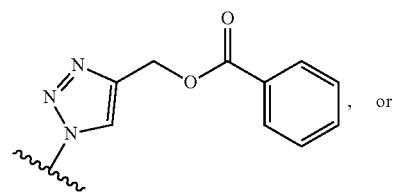

-continued

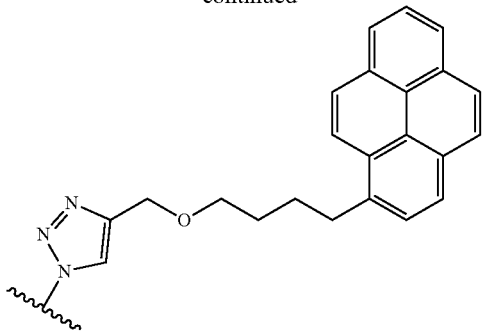

In some cases, the absorbent material may include an iptycene-based polymer. For example, the iptycene-based polymer may include one or more of the following groups.

Figure 13:
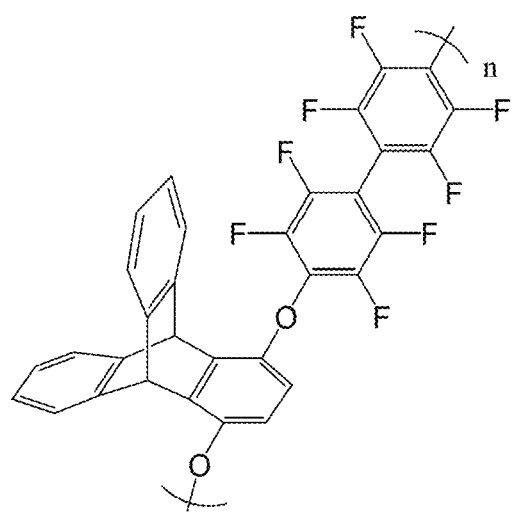
FIG. 13 shows an example of an iptycene-containing polymer used in a sensor coating.
Figure 13:
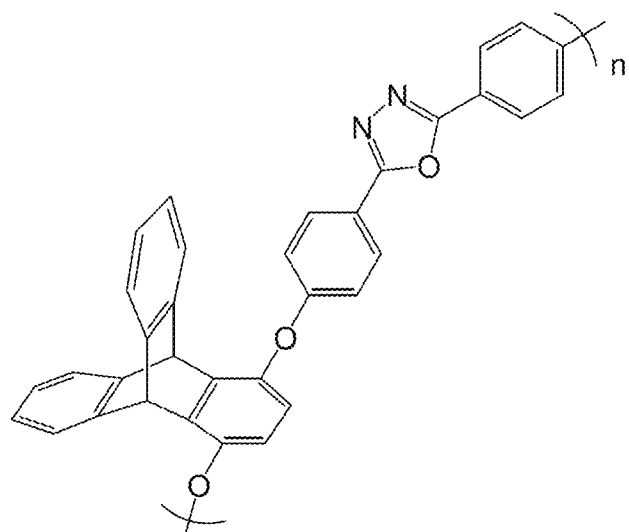
Figure 13:
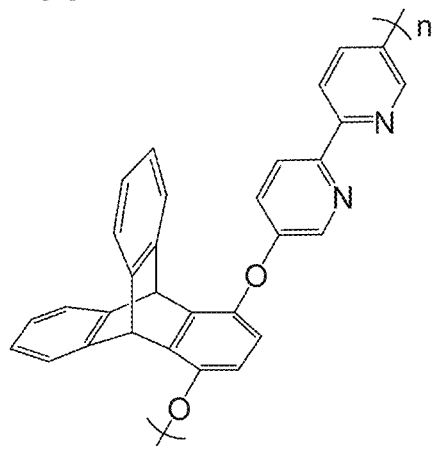

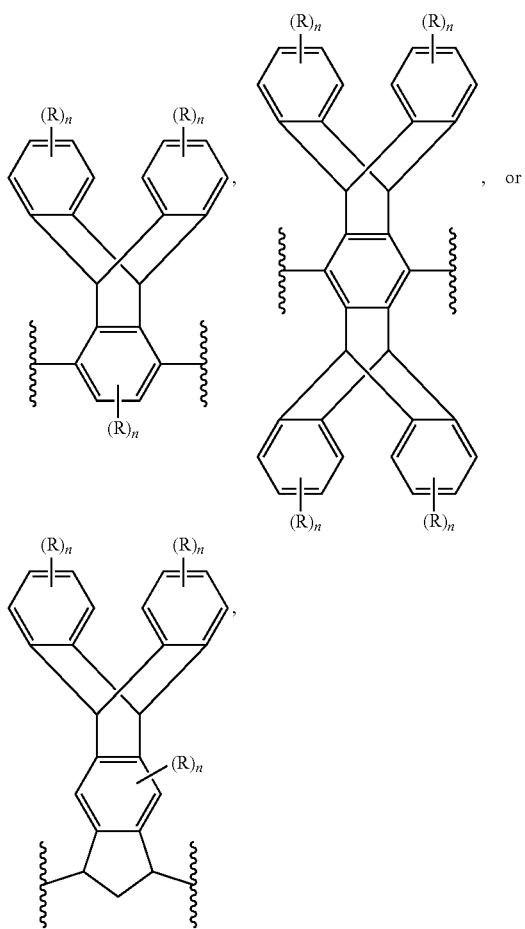

wherein each R can be the same or different and is H or a substituent (e.g., an organic substituent) and n is an integer between 0 and 4. In some cases, each R is independently selected from H, halide, or an organic group (e.g., an organic side chain). In some cases, at least one R is a group comprising a binding site as described herein. In some cases, the iptycene-based polymer may include a conjugated polymer backbone (e.g., pi-conjugated polymer backbone), such as polyarylenes, poly(arylene vinylene)s, poly(arylene ethynylene)s, and the like. In some cases, the iptycene-based polymer may include a non-conjugated polymer, such as polyethers, polysulfones, polycarbonates, polyacrylates, and the like. FIGS. 10 and 13 show examples of some iptycene-based polymers.

Some specific examples of absorbent materials include polystyrene, poly(ethylene:vinyl acetate+vinyl chloride) ("Saran wrap"), paraffin film ("Parafilm"), silicon grease, polyethylene, poly(vinyl chloride), fluorinated polymers including CYTOP A and CYTOP S (Bellex International Corp.), poly(chlorotrifluoroethylene)s (e.g., Halocarbon oil 27, Halocarbon oil 700), and polytetrafluoroethylenes (e.g., Teflon AF2400), various polymers shown in the Figures, and the like.

In some cases, the absorbent material may include an ionic liquid. Based on the teachings of this disclosure, those of ordinary skill in the art can readily select ionic liquids suitable for use in the invention. Those ionic liquids that are suitable typically will be capable of absorbing an analyte. In certain embodiments, the ionic liquid comprises an anion and/or a cation. Non-limiting examples of suitable anions include tetrafluoroborate, hexafluorophosphate, hexafluoroarsenoate, perchlorate, trifluoromethanesulfonate, bis(trifluoromethylsulfonyl)amide, and thiosaccharin anion. Non-limiting examples of suitable cations include ammonium, imidazolium, pyridinium, piperidinium and pyrrolidinium derivatives. The ionic liquid can, in some embodiments, include a combination of any one of the above anions and any one of the above cations. For example, in some embodiments, the ionic liquid comprises an imidazolium ion (e.g., a substituted imidazolium ion). Non-limiting examples of imidazolium ions include 1-Butyl-3-methylimidazolium, 1-Ethyl-3-methylimidazolium, and 1-Hexyl-3-methylimidazolium. In some cases, the counterion of the imidazolium ion may be tetrafluoroborate, hexafluorophosphate, or bis (trifluoromethanesulfone)imide.

In some embodiments, the absorbent material includes two or more materials (e.g., a first absorbent material (e.g. an ionic liquid) and a second absorbent material (e.g., a polymer)). In certain embodiments, the first absorbent material is adjacent the second absorbent material (e.g., an ionic liquid layer adjacent a polymeric layer). In some cases, the first absorbent material may be mixed with the second absorbent material (e.g., an ionic liquid mixed with a polymer, an ionic liquid absorbed within a polymer).

Absorbent materials described herein may be synthesized using various methods known in the art. In the case of absorbent materials, the polymers may be synthesized according to known methods, including, but not limited to, cationic polymerization, anionic polymerization, radical polymerization, condensation polymerization, Wittig polymerization, ring-opening polymerization, cross-coupling polymerization, addition polymerization, chain polymerization, metathesis polymerization, or the like. Those of ordinary skill in the art would be able to select the appropriate monomers in order to obtain a desired polymeric product. For example, monomers comprising two hydroxyl groups may be polymerized with monomers comprising two carbonyl groups (e.g., acyl halide, carboxylic acid, etc.) to form a polyether via condensation polymerization. Likewise, monomers comprising a styrene moiety may be polymerized to form polystyrene via radical polymerization. In one embodiment, monomers comprising di-acetylene substituted aryl groups may be polymerized with monomers comprising di-halide substituted aryl groups to form poly (arylene ethynylene)s via cross-coupling polymerization.

In some embodiments, a plurality of devices may be arranged to form an array of devices capable distinguishing, identifying, and quantifying a variety of different analytes simultaneously. For example, in an array of devices, each individual device can include a binding site capable of interacting with an analyte. In some cases, a first device of the array may include a binding site capable of interacting with a first analyte and a second device of the array may include a binding site capable of interacting with a second analyte, wherein the first and second analytes are different.

In some embodiments, a single device may include a mixture of different binding sites capable of determining a plurality of different analytes.

The absorbent material may include additional components for improving the interaction between an analyte and the absorbent material, the interaction between the absorbent material and the sensor material, the response of the sensor material to the analyte, the stability of the absorbent material and/or sensor material, or otherwise enhancing the performance of the device. For example, the sensor material layer and/or absorbent material layer may include one or more species capable of interacting with the analyte. The species may be selected to be responsive to a particular analyte, set of analytes, and/or to a change in a set of conditions in the surrounding environment, and may be integrally connected to the absorbent material and/or sensor material. As used herein, the term "integrally connected," when referring to two or more components, means components that do not become separated from each other during the course of normal use, e.g., separation requires at least the use of tools, or by breaking bonds, by dissolving, etc. In some cases, the species may be any of the binding sites described herein.

In some embodiments, the absorbent material may be associated with species capable of interacting with analytes (e.g., binding sites). The species may be attached to the absorbent material via, for example, covalent bonds. In some cases, the species may be associated with the absorbent material via non-covalent bonds. In some cases, the species may be substantially dispersed throughout the polymer material.

In some embodiments, the species may be capable of migrating from one component of the device to another component. For example, the species may be non-covalently dispersed throughout an absorbent material layer (e.g., "loaded" onto the absorbent material) and may migrate or diffuse to a sensor material layer in contact with the absorbent material layer. The species may then facilitate or enhance the performance of the sensor material layer in responding to the presence of an analyte. In some cases, the sensor material layer may include a particular species, and an absorbent material layer disposed on the sensor material layer may contain an amount of the same species, which can migrate to the absorbent material layer. In this arrangement, the absorbent material layer can serve as a reservoir for excess species to be delivered to the sensor material layer, if needed. For example, the species in the sensor material may be consumed, may degrade, or may otherwise become depleted during operation. In another set of embodiments, the sensor material layer may include a particular species, and an absorbent material layer disposed on the sensor material layer may contain an amount of a different species, which can migrate to the absorbent material layer. This may allow for devices which are capable of determining more than one type of analyte.

In some cases, the sensor material (e.g., sensor material layer) may include carbon-based nanostructures as the conductive material. For example, the conductive material may include nanotubes, nanoparticles, graphene, or graphite. In some embodiments, the conductive material includes nanotubes. In some embodiments, the conductive material includes single-wall carbon nanotubes. In some embodiments, the conductive material includes multi-wall carbon nanotubes. In some embodiments, the conductive material includes graphite. In some embodiments, the conductive material includes graphene.

In one set of embodiments, the conductive material may be single-wall carbon nanotubes (SWCNTs) and functionalized cellulose acetate (CA) may be employed as a the absorbent material (e.g., "preconcentrator") that selectively absorbs the analyte of interest.

In some cases, arranging an absorbent material layer in contact with the sensor material may improve the physical, chemical, and mechanical stability of the sensor material, or other components of the sensor material. For example, undesired phase separation between the absorbent material and the conductive material may be reduced or avoided.

Polymers may be substituted with various binding sites using methods known in the art. In some cases, a polymer containing one or more hydroxyl functional groups may be utilized as starting material. In some cases, the hydroxyl functional group may be an alcohol (e.g., a primary alcohol, secondary alcohol, tertiary alcohol). The hydroxyl group may then be functionalized using various chemical reactions known in the art, including esterification. Cellulose-based polymers contain a plurality of hydroxyl functional groups that may be functionalized with binding sites.

Figure 7A:
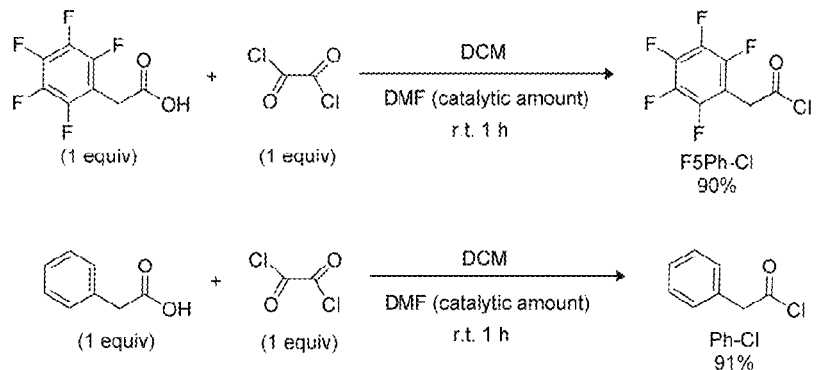
FIGS. 7A-7B shows (FIG. 7A) the syntheses of pentafluorophenylacetyl chloride (F5Ph-Cl) and phenyacetyl chloride (Ph-Cl) and (FIG. 7B) functionalization of cellulose acetate with F5Ph-Cl and Ph-Cl receptors via esterification.
Figure 7B:
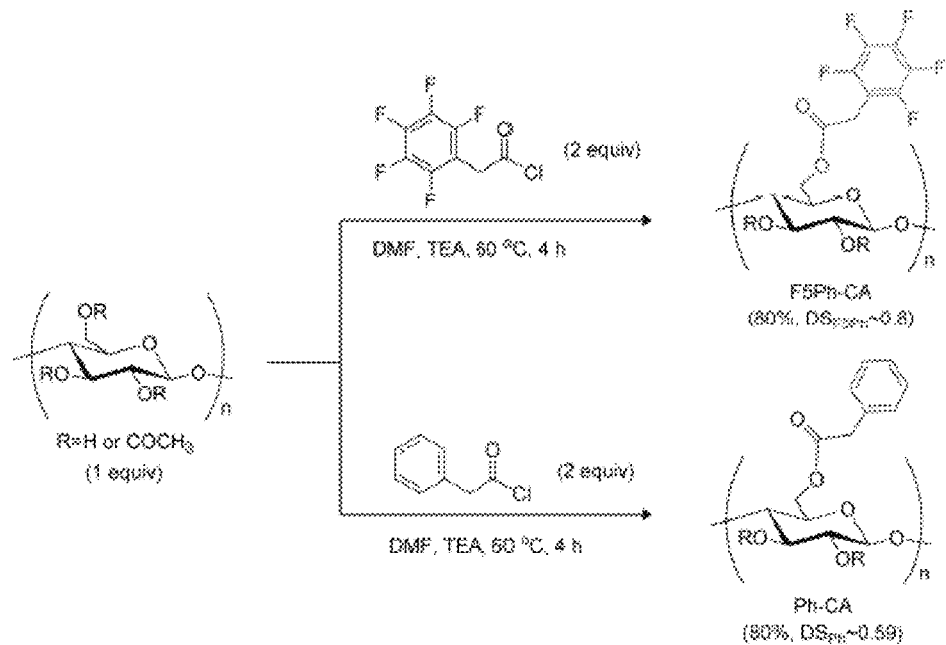

In one set of embodiments, a polymer containing hydroxyl groups may be functionalized using an esterification reaction. For example, the polymer may be reacted with a binding site precursor containing a functional group that can react with the hydroxyl group of the polymer via an esterification reaction. In some cases, the functional group may be an acid chloride. The esterification reaction may be catalyzed by an acid (e.g., acetic acid) or a base (e.g., triethylamine). In other embodiments, a polymer may include a hydroxyl group which may be treated with a binding site precursor, a phosphine (e.g., triphenylphosphine, TPP), and diethylazodicarboxylate (DEAD) or diisopropyl azodicarboxylate (DIAD) under Mitsunobu reaction conditions to form an ester. Those of ordinary skill in the art would be capable of selecting the appropriate combination of polymer, binding site precursor, and esterification reaction conditions suitable for a particular desired product. FIG. 7 shows one embodiment where 2,3,4,5,6-pentafluorophenylacetyl- and phenylacetyl-functionalized cellulose acetates (F5Ph-CA and Ph-CA) may be synthesized by esterification reaction of cellulose acetates with 2,3,4,5,6-pentafluorophenylacetyl chloride and phenylacetyl chloride in the presence of triethylamine, respectively.

Figure 6A:
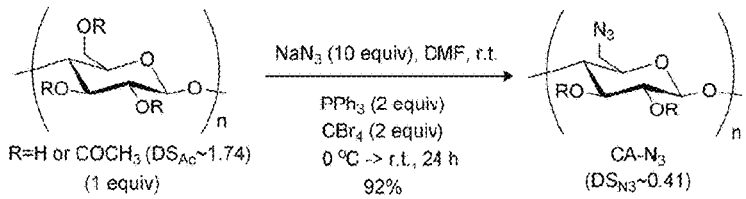
FIGS. 6A-6B shows synthetic schemes for (FIG. 6A) 6-deoxy-6-azido cellulose acetate (CA-N3) via one pot azidation and (FIG. 6B) copper(I)-catalyzed azide-alkyne cycloaddition reaction (CuAAC) of 6-deoxy-6-azido cellulose acetate with propargyl receptors.
Figure 6B:
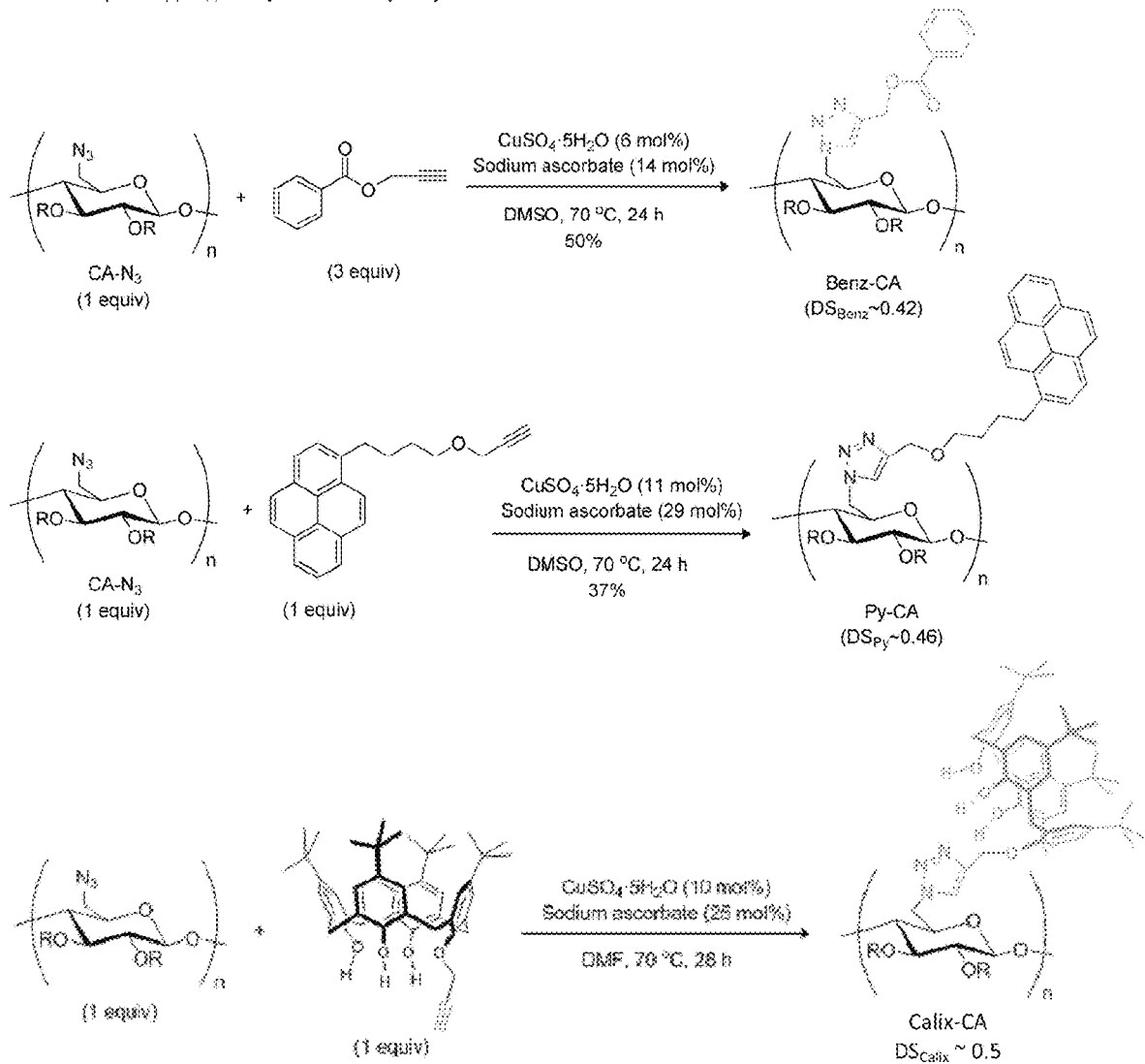

In one set of embodiments, a polymer containing hydroxyl groups may be reacted to form a moiety capable of reacting via a 1,3-dipolar cycloaddition reaction, i.e., via "click chemistry." For example, a primary alcohol may be converted to an azide group by treatment with sodium azide, and the azide group may be reacted with a binding site precursor containing a dipolarophile group (e.g., an alkyne) via a cycloaddition reaction. In some embodiments, the cycloaddition reaction may be catalyzed by a metal such as copper. FIG. 6 shows one embodiment where cellulose acetate with the degree of substitution of acetyl groups (DSAc) of 1.74 is used as a starting material. Pyrene- and benzoate-functionalized cellulose acetates (Py-CA and Benz-CA) may be synthesized via copper (I)-catalyzed azide-alkyne cycloaddition (CuAAC) reaction between propargyl pyrenebutyl ether and benzoate and 6-deoxy-6-azido cellulose acetates, respectively.

In some embodiments, a cellulose-based polymer may be functionalized with various binding sites using methods described herein.

An analyte, or a change in the environment surrounding the device, may be determined by monitoring, for example, a change in a signal of a species or material present within the device. The change in signal may be associated with an interaction (e.g., covalent bonding, non-covalent bonding) between the device (e.g., species) and the analyte. The signal may comprise an electrical, optical, or other property of the device. For example, the device may have a resistance that is affected by the presence of an analyte. As used herein, the term "determining" generally refers to the analysis of a species or signal, for example, quantitatively or qualitatively (whether the analyte is present and/or in what amount or concentration), and/or the detection of the presence or absence of the species or signals. "Determining" may also refer to the analysis of an interaction between two or more species or signals, for example, quantitatively or qualitatively, and/or by detecting the presence or absence of the interaction. For example, the method may include the use of a device capable of producing a first, determinable signal (e.g., a reference signal), such as an electrical signal, an optical signal, or the like, in the absence of an analyte. The device may then be exposed to a sample suspected of containing an analyte, wherein the analyte, if present, may interact with one or more components of the device to cause a change in the signal produced by the device. Determination of the change in the signal may then determine the analyte. In some cases, devices described herein may be useful as sensors for analytes such as explosives, chemical warfare agents, and/or toxins. In some cases, the analyte may be an aromatic species such as benzene, toluene, xylene, or benzo[a]pyrene.

In some embodiments, interaction between the device and an analyte produces a change in an electrical or electrochemical property of the device. For example, the conductive material (e.g., carbon nanotube) may be arranged in electrical communication with two electrodes and may have a particular current, voltage, conductivity, and/or resistance (e.g., signal). Upon interaction with an analyte, the current, voltage, conductivity, and/or resistance of the device may be affected (e.g., may increase or decrease) such that a change in signal is produced. In some cases, the change in signal may be associated with a charge transfer reaction and/or binding interaction between the conductive material and the analyte. In some cases, the change in the signal may be associated with a change in the orientation and/or arrangement of the conductive material. In some cases, the change in signal may be attributed to a physical or chemical disruption in the conductive pathways between conductive species (e.g., carbon nanotubes) of the device. In some cases, the conductive species and the absorbent material may have an interaction (e.g., pi-pi interaction) and the change in signal may be attributed to a physical or chemical disruption of the interaction.

In an illustrative embodiment, the device may be exposed to an analyte, which may interact with the absorbent material (e.g., absorbent material) such that the analyte intercalates within (or is absorbed by) the absorbent material to produce a concentrated amount of analyte within the absorbent material. The analyte may diffuse through the absorbent material to a location that is sufficiently proximate the sensor material so as to cause a change in signal produced by the sensor material. That is, the analyte may be present in sufficient physical proximity to the sensor material, and/or in a sufficient concentration, to cause a change in signal produced by the sensor material.

In some cases, resistance to current flow between the first and second electrode is increased in the presence of the analyte. In some cases, resistance to current flow between the first and second electrode is decreased in the presence of the analyte.

Incorporation of an absorbent material within devices described herein may improve device performance, relative to an essentially identical device lacking the absorbent material, under essentially identical conditions. In some cases, the device containing an absorbent material may, in response to an analyte, produce a signal that is 2, 5, 10, 50, 100, 500, or 1000 times greater than a signal produced by an essentially identical device lacking the absorbent material, under essentially identical conditions.

In some cases, the device may comprise additional components or species that may facilitate interaction between the device and analyte, or otherwise enhance performance of the device. In some cases, the additional component may improve the ability of the device to produce a signal or to respond to an analyte. The additional component may associate with the device such that it enhances an electrical, optical, or other property of the device. In some cases, the additional component may act as a dopant for a conductive species (e.g., carbon nanotube) present within the device. For example, the device may comprise a species capable of associating with carbon nanotubes present within the device. In some embodiments, the device includes a species that may interact with the carbon nanotubes via pi-stacking interactions.

The device may comprise additional components, such as a detector component positioned to detect the signal. In one set of embodiments, the device may be a chemiresistor device, wherein the device exhibits changes in electrical resistance upon exposure to an analyte. Chemiresistors may be advantageous in that the resistance changes can be read-out by a simple, low power and low current circuit. In other embodiments, a device of the present invention may exhibit signals, or changes in signals, that may be determined using Raman spectroscopy, adsorption and/or emission photophysics, ellipsometry, atomic force microscopy, scanning electron microscopy, electrode passivation, and the like.

In some embodiments, simple screening tests may be conducted to select appropriate absorbent materials, conductive materials (e.g., carbon nanotubes), binding sites, device configuration, set of conditions, etc., to suit a particular application. In some cases, a material or device may be screened to determine the sensitivity and/or stability of the material or device. In some cases, a material (and/or device) may be selected based on an ability to detect one or more analytes. For example, the ability of a device to detect an analyte may be determined by comparing the signal (e.g., resistance) of the device prior to and following exposure to an analyte. In another example, a device may be exposed to varying concentrations of an analyte to determine the sensitivity of the device.

Devices described herein may be useful in various applications including environmental monitoring and leak detection in chemical and petrochemical industries. In some embodiments, the device may be configured as a surface acoustic wave (SAW) sensor including an absorbent material as described herein. Such devices may include additional components in order to facilitate the transduction mechanism of a SAW device. For example, the SAW sensor may further include a piezoelectric material. In some cases, the absorbent material may be incorporated into a surface plasmon device. In some embodiments, the device may lack a piezoelectric material.

Methods for determining analytes are also provided. Typically, the method involves exposure of a sample suspected of containing an analyte to a device as described herein. In some cases, the sample is a vapor sample. The absorbent material may serve as a preconcentrator for the analyte sample. That is, the absorbent may have a first analyte concentration prior to exposure to the sample and a second, increased analyte concentration upon exposure to the sample. In some cases, a determinable signal (e.g., resistance) produced by the sensor material may be affected by the presence of the analyte. In some cases, the absorbent material may also interact with the analyte in a manner bringing the analyte into proximity with the sensor material to affect the determinable signal of the device.

In some cases, methods for fabricating the devices described herein are also provided. The method may involve, for example, forming a sensor material on a substrate, followed by forming an absorbent material on the sensor material to form a layered structure. The substrate may include additional components, including electrodes formed on the surface of the substrate such that the sensor material may be in physical contact with, or at least electrical communication with, the electrode. The materials may be formed using a variety of known methods, including drop-casting, spin-coating, spray-coating, inkjet or screen printing, and the like. For example, a solution containing the sensor material and/or absorbent material and a fluid carrier may be spun-cast or drop-cast on the surface of a substrate, and the fluid carrier (e.g., solvent) may be removed to form a substantially solid film or layer. In some cases, the sensor material and absorbent material may be formed as separate layers, i.e., using a first solution containing the sensor material to form a first layer and a second solution containing the absorbent material to form a second layer. In some cases, the sensor material and absorbent material may be formed as a single layer. e.g., using a solution containing the sensor material and the absorbent material.

The fluid carrier may be an organic solvent, including acetone, toluene, benzene, tetrahydrofuran, dimethylformamide, hexanes, dimethylsulfoxide, ethyl acetate, acetonitrile, dichloromethane, chloroform, carbon tetrachloride, and fluorinated solvents including perfluorocarbons (e.g., perfluorohexane, perfluoromethylcyclohexane, perfluorodecalin) and hydrofluoroethers. Some specific examples of fluorinated solvents include perfluorohexane, hexafluorobenzene), and CT-SOLV 180 (Bellex International Corp.). In some cases, the absorbent material (e.g., polymer absorbent material) may be combined with a fluid carrier at a concentration in the range of about 0.1 mg/mL to about 100 mg/mL. The resulting solution may then be spin-cast, drop-cast, or otherwise processed, to form a layer comprising the absorbent material.

In an illustrative embodiment, a metal electrode (e.g., gold) may be patterned, evaporated, or otherwise formed on the surface of a substrate (e.g., a glass substrate). A first layer containing the sensor material may be formed on the substrate, followed by a second layer formed on the first layer and containing the absorbent material. The conductive material may be any material capable of conducting charge, including inorganic materials (e.g., metals, alloys, semiconductors), organic materials, organometallic materials, and/or combinations thereof. For example, the conductive material may include nanostructures (e.g., nanotubes, nanoparticles, graphene, etc.), polymers (e.g., conductive polymers), metal-containing species (e.g., metals, metal salts, etc.), biological species (e.g., proteins, DNA, RNA, etc.), and/or small molecules. In some cases, the conductive material comprises a carbon-based material such as a carbon-based nanostructure (e.g., carbon nanotubes, graphite, or graphene). In some embodiments, the conductive material comprises carbon nanotubes, including single-walled carbon nanotubes and/or multi-walled carbon nanotubes. In some cases, the conductive material may be a conjugated polymer (e.g., pi-conjugated, sigma-conjugated), including iptycene-based conjugated polymers (e.g., triptycene-based conjugated polymers, pentiptycene-based conjugated polymers).

"Electrochemical communication," as used herein, refers to materials that are in sufficient communication with each other, such that the transfer of electrons, polarons, excitons, and/or protons can occur between the two materials. For example, the first and second electrodes may not physically contact one another but may be in electrochemical communication with one another via the conductive material, such that upon application of a voltage or potential, a current flows from the one electrode through the conductive material to the other electrode.

As used herein, the term "nanostructure" refers to any chemical structure having at least one dimension on the order of nanometers. In some cases, the nanostructure has an elongated chemical structure having a diameter on the order of nanometers and a length on the order of microns to millimeters, resulting in an aspect ratio greater than 10, 100, 1000, 10,000, or greater. In some cases, the nanostructure may have a diameter less than 1 μm, less than 100 nm, 50 nm, less than 25 nm, less than 10 nm, or, in some cases, less than 1 nm. The nanostructure may have a cylindrical or pseudo-cylindrical shape. In some cases, the nanostructure may be a nanotube, such as a carbon nanotube. In some cases, the nanostructure is a nanorod, nanowire, or nanoribbon. In some cases, the nanostructure is a nanoparticle.

As used herein, the term "carbon nanotube" is given its ordinary meaning in the art and refers to a substantially cylindrical molecule, in some cases, comprising a fused network of six-membered aromatic rings. In some cases, carbon nanotubes may resemble a sheet of graphite rolled up into a seamless cylindrical structure. It should be understood that the carbon nanotube may also comprise rings other than six-membered rings. Typically, at least one end of the carbon nanotube may be capped, i.e., with a curved or nonplanar aromatic group. Carbon nanotubes may have a diameter of the order of nanometers and a length on the order of millimeters, resulting in an aspect ratio greater than about 100, greater than about 1000, greater than about 10,000, or greater. The term "carbon nanotube" includes single-walled nanotubes (SWCNTs), multi-walled nanotubes (MWCNTs) (e.g., concentric carbon nanotubes), inorganic derivatives thereof, and the like. In some embodiments, the carbon nanotube is a single-walled carbon nanotube. In some cases, the carbon nanotube is a multi-walled carbon nanotube (e.g., a double-walled carbon nanotube).

The carbon nanotubes may be functionalized or substituted with a wide range of functional groups. Examples of functional groups that carbon nanotubes may be substituted with include peptides, proteins, DNA, RNA, peptide nucleic acids (PNA), metal complexes, ligands for metals, ligands for proteins, antibodies, polarizable aromatics, crown ethers, hydroxyl amines, polymers, initiators for polymerizations, liquid crystals, fluorocarbons, synthetic receptors, and the like. The properties of the nanotubes may also be tailored based on the substitution of the fused, aromatic network. Those skilled in the art would recognize what types of functional groups would afford a particular, desired property, such as increased solubility, or the ability to determine an analyte.

Substituted carbon nanotubes may be synthesized using various methods, including those described in Zhang et al., J. Am. Chem. Soc. 2007, 129(25), 7714; International Publication No. WO2008/133779, which are incorporated herein by reference in their entirety for all purposes.

In some cases, the conductive material may comprise nanoparticles. As used herein, the term "nanoparticle" generally refers to a particle having a maximum cross-sectional dimension of no more than 1 μm. Nanoparticles may comprise inorganic or organic, polymeric, ceramic, semiconductor, metallic, non-metallic, magnetic, crystalline (e.g., "nanocrystals"), or amorphous material, or a combination of two or more of these. The nanoparticles may be also selected to be positively or negatively charged. Typically, nanoparticles may have a particle size less than 250 min in any dimension, less than 100 nm in any dimension, or less than 50 nm in any dimension. In some embodiments, the nanoparticles may have a diameter of about 2 to about 50 nm. In some embodiments, the nanoparticles may have a diameter of about 2 to about 20 nm. The particle size may be measured by methods known in the art, such as electron microscopy.

Polymers or polymeric materials, as used herein, refer to extended molecular structures comprising a backbone (e.g., non-conjugated backbone, conjugated backbone) which optionally contain pendant side groups, where "backbone" refers to the longest continuous bond pathway of the polymer. In some embodiments, the polymer is substantially non-conjugated or has a non-conjugated backbone. In some embodiments, at least a portion of the polymer is conjugated, i.e. the polymer has at least one portion along which electron density or electronic charge can be conducted, where the electronic charge is referred to as being "delocalized." A polymer may be "pi-conjugated," where atoms of the backbone include p-orbitals participating in conjugation and have sufficient overlap with adjacent conjugated p-orbitals. It should be understood that other types of conjugated polymers may be used, such as sigma-conjugated polymers.

The polymer can be a homo-polymer or a co-polymer such as a random co-polymer or a block co-polymer. In one embodiment, the polymer is a block co-polymer. An advantageous feature of block co-polymers is that they may mimic a multi-layer structure, wherein each block may be designed to have different band gap components and, by nature of the chemical structure of a block co-polymer, each band gap component is segregated. The band gap and/or selectivity for particular analytes can be achieved by modification or incorporation of different polymer types, as would be understood by those of ordinary skill in the art. The polymer compositions can vary continuously to give a tapered block structure and the polymers can be synthesized by either step growth or chain growth methods.

The number average molecular weight of the polymer may be selected to suit a particular application. As used herein, the term "number average molecular weight (Mn)" is given its ordinary meaning in the art and refers to the total weight of the polymer molecules in a sample, divided by the total number of polymer molecules in a sample. Those of ordinary skill in the art will be able to select methods for determining the number average molecular weight of a polymer, for example, gel permeation chromatography (GPC). In some cases, the GPC may be calibrated vs. polystyrene standards. In some cases, the number average molecular weight of the polymer is at least about 10,000, at least about 20,000, at least about 25,000, at least about 35,000, at least about 50,000, at least about 70,000, at least about 75,000, at least about 100,000, at least about 110,000, at least about 125,000, or greater.

The device may also comprise an insulating material. The insulating material may be arranged between the conductive material and one or more electrodes and/or the substrate. Examples of suitable insulating materials include, but are not limited to, polysilicate glass, silicon dioxide, silicon nitride, and the like.

As used herein, the term "electrode" or "electrode material" refers to a composition, which, when connected to an electronic device, is able to sense a current or charge and convert it to a signal. An electrode may be comprised of a conductive material or combination of materials such as, for example, metals. Non-limiting examples of suitable metals include gold, copper, silver, platinum, nickel, cadmium, tin, and the like. The electrodes may also be any other metals and/or non-metals known to those of ordinary skill in the art as conductive (e.g. ceramics). The electrodes may be deposited on a surface via vacuum deposition processes (e.g., sputtering and evaporation), solution deposition (e.g., electroplating or electroless processes), or screen printing. In a specific example, gold electrodes are deposited by thermal evaporation. In another embodiment, gold electrodes are screen printed on a surface.

In some embodiments, the conductive material may comprise a conductive, semiconductive, semimetallic species, or other species capable of transporting charge to create a conductive pathway. The conductive, semiconductive, or semimetallic species may include inorganic materials (e.g., metals, alloys, semiconductors), organic materials (e.g., polymer materials), organometallic materials, and/or combinations thereof. In some cases, the conductive material may include a plurality of nanostructures (e.g., nanotubes, nanowires, nanoribbons, nanoparticles, etc.). The nanostructures may be selected to exhibit, for example, high charge mobilities and/or resistance to damage from ionizing radiation. In some cases, mixtures or assemblies of nanostructures may be utilized. Some embodiments may involve the use of carbon nanotubes, such as single-walled carbon nanotubes (SWCNTs) and/or multi-walled carbon nanotubes (MWCNTs), which can display relatively high charge mobilities (e.g., 100,000 cm2/Vs for SWCNTs). In some cases, nanowires, such as gold, silver, copper, bismuth, gadolinium nanowires, may be used as the conductive species. In some cases, the conductive, semiconductive, or semimetallic species may comprise nanoparticles (e.g., gold nanoparticles).

As used herein, an "analyte" can be any chemical, biochemical, or biological entity (e.g. a molecule) to be analyzed. The analyte may be in vapor phase, liquid phase, or solid phase. In some embodiments, the analyte is a vapor phase analyte. In some cases, the analyte may be a form of electromagnetic radiation. In some cases, the device may be selected to have high specificity for the analyte, and may be a chemical, biological, or explosives sensor, for example. In some embodiments, the analyte comprises a functional group that is capable of interacting with at least a portion of the device (e.g., a species). In some cases, the device may determine changes in pH, moisture, temperature, and the like, of a surrounding medium. The analyte may be a chemical species, such as an explosive (e.g., TNT), toxin, or chemical warfare agent. In a specific example, the analytes are chemical warfare agents (e.g., sarin gas) or analogs of chemical warfare agents (e.g., dimethyl methylphosphonate, DMMP).

In some embodiments, the analyte may be an aromatic species, including optionally substituted aryl species and/or optionally substituted heteroaryl species, such as benzene, toluene, xylene, or polycyclic aromatic hydrocarbons such as benzo[a]pyrene. In some embodiments, the analyte may be an amine-containing species such as ammonia. In some embodiments, the analyte may be a nitrile-containing species such as acetonitrile. In some embodiments, the analyte may be an oxygen-containing species, such as a species comprising an alcohol, a ketone, an ester, a carboxylate, an aldehyde, other carbonyl groups, an ether, or the like. In some embodiments, the analyte may be a species comprising a ketone, an ester, an ether, or an aldehyde, such as cyclohexanone, ethyl acetate, THF, or hexanal. In some embodiments, the analyte is a phosphorus-containing analyte such as DMMP. In some embodiments, the analyte may be a nitro-containing species such as nitromethane or TNT. Other examples of analytes include alcohols, olefins, nitric oxide, thiols, thioesters, and the like.

Specific examples of analytes include nitromethane, benzene, toluene, o-xylene, m-xylene, p-xylene, mesitylene, nitrobenzene, cyano-benzene, benzo[a]pyrene, hexane, hexene, hexenal, ethylene, 1-methylcyclopropene, propene, butenes, isoprene, cyclohexanone, acetone, tetrahydrofuran (THF), methanol, ethanol, isopropanol, hexanal, DMMP, acetonitrile, nitromethane, ethyl acetate, methyl acetate, water, dimethylformamide (DMF), formaldehyde, dimethylsulfide, ethylene, or ammonia.

In some cases, the device may determine changes in a condition, or set of conditions, of a surrounding medium. As used herein, a change in a "condition" or "set of conditions" may comprise, for example, change to a particular temperature, pH, solvent, chemical reagent, type of atmosphere (e.g., nitrogen, argon, oxygen, etc.), electromagnetic radiation, or the like. In some cases, the set of conditions may include a change in the temperature of the environment in which the device is placed. For example, the device may include a component (e.g., binding site) that undergoes a chemical or physical change upon a change in temperature, producing a determinable signal from the device.

As used herein, an "aromatic species" includes unsubstituted or substituted, monocyclic or polycyclic aromatic ring or ring radical, including unsubstituted or substituted monocyclic or polycyclic heteroaromatic rings or ring radicals (e.g., aromatic species including one or more heteroatom ring atoms). Examples of aromatic species include phenyl, naphthyl, anthracenyl, chrysenyl, fluoranthenyl, fluorenyl, phenanthrenyl, pyrenyl, perylenyl, and the like.

As used herein, "aryl" means a monocyclic or polycyclic-aromatic ring or ring radical comprising carbon and hydrogen atoms. Examples of suitable aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or more substituents (including without limitation alkyl (preferably, lower alkyl or alkyl substituted with one or more halo), hydroxy, alkoxy (preferably, lower alkoxy), alkylthio, cyano, halo, amino, and nitro.

As used herein, "heteroaryl" means a monocyclic or polycyclic heteroaromatic ring (or radical thereof) comprising carbon atom ring members and one or more heteroatom ring members (such as, for example, oxygen, sulfur or nitrogen). Typically, the heteroaromatic ring has from 5 to about 14 ring members in which at least 1 ring member is a heteroatom selected from oxygen, sulfur, and nitrogen. In another embodiment, the heteroaromatic ring is a 5 or 6 membered ring and may contain from 1 to about 4 heteroatoms. In another embodiment, the heteroaromatic ring system has a 7 to 14 ring members and may contain from 1 to about 7 heteroatoms. Representative heteroaryls include pyridyl, furyl, thienyl, pyrrolyl, oxazolyl, imidazolyl, indolizinyl, thiazolyl, isoxazolyl, pyrazolyl, isothiazolyl, pyridazinyl, pyrimidinyl, pyrazinyl, triazinyl, triazolyl, pyridinyl, thiadiazolyl, pyrazinyl, quinolyl, isoquniolyl, indazolyl, benzoxazolyl, benzofuryl, benzothiazolyl, indolizinyl, imidazopyridinyl, isothiazolyl, tetrazolyl, benzimidazolyl, benzoxazolyl, benzothiazolyl, benzothiadiazolyl, benzoxadiazolyl, indolyl, tetrahydroindolyl, azaindolyl, imidazopyridyl, qunizaolinyl, purinyl, pyrrolo[2,3]pyrimidyl, pyrazolo[3,4]pyrimidyl, benzo(b)thienyl, and the like. These heteroaryl groups may be optionally substituted with one or more substituents.

The term "substituted" is contemplated to include all permissible substituents of organic compounds, "permissible" being in the context of the chemical rules of valence known to those of ordinary skill in the art. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" must still comprise the phenyl moiety and cannot be modified by substitution, in this definition, to become, e.g., a heteroaryl group such as pyridine. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, alkyl, aryl, aralkyl, cyclic alkyl, heterocycloalkyl, hydroxy, alkoxy, aryloxy, perhaloalkoxy, aralkoxy, heteroaryl, heteroaryloxy, heteroarylalkyl, heteroaralkoxy, azido, amino, halogen, alkylthio, oxo, acylalkyl, carboxy esters, carboxyl, carboxamido, nitro, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, alkoxyalkyl, perhaloalkyl, arylalkyloxyalkyl, and the like.

Other embodiments suitable for use in the context of the embodiments described herein are described in International Pat. Apt. Serial No.: PCT/US2009/001396, filed Mar. 4, 2009, entitled. "Devices and Methods for Determination of Species Including Chemical Warfare Agents"; International Pat. Apl. Serial No.: PCT/US2009/006512, filed Dec. 11, 2009, entitled, "High Charge Density Structures, Including Carbon-Based Nanostructures and Applications Thereof"; U.S. patent application Ser. No. 12/474,415, filed May 29, 2009, entitled, "Field Emission Devices Including Nanotubes or Other Nanoscale Articles"; International Pat. Apl.

Serial No.: PCT/US2011/051610, filed Oct. 6, 2010, entitled, "Method and Apparatus for Determining Radiation"; International Pat. Apl. Serial No.: PCT/US2010/055395, filed Nov. 4, 2010, entitled, "Nanostructured Devices including Analyte Detectors, and Related Methods"; International Pat. Apl. Serial No.: PCT/US2011/053899, filed Sep. 29, 2011, entitled, "COMPOSITIONS, METHODS, AND SYSTEMS COMPRISING POLY (THIOPHENES); and International Pat. Apl. Serial No.: PCT/US2011/025863, filed Feb. 23, 2011, entitled, "Charged Polymers and Their Uses in Electronic Devices", which applications are incorporated herein in their entireties for all purposes.

EXAMPLES AND EMBODIMENTS

Materials and Measurements. Chemicals were purchased from Sigma-Aldrich, Alfa Aesar, and Macron Chemicals and used as received except that THF was dried by distillation. Deuterated solvents for NMR were obtained from Cambridge Isotope Laboratories, Inc. Cellulose acetate (CA-320S NF/EP) with the acetyl content of 31.9 wt % was kindly provided from Eastman. The analytes including benzene, toluene, ortho-, meta-, and para-xylenes, ethanol, and n-heptane were reagent grade and used as received.

$^1$H, $^{13}$C, and $^{19}$F NMR spectra were recorded on Varian Mercury (300 MHz) and Inova (500 MHz) NMR spectrometers. The $^{13}$C NMR spectra for functionalized cellulose acetates were recorded at 60° C. Chemical shifts are reported in parts per million (ppm) and referenced to the residual solvent resonance. FT-IR spectra were obtained on a NICO-LET 6700 FT-IR (Thermo Scientific) in attenuated total reflectance (ATR) mode using a Ge crystal plate. Thermal stabilities of functionalized cellulose acetates were studied using a thermogravimetric analysis (TGA, Discovery TGA from TA Instruments). Weight loss was monitored by heating a sample from 30° C. to 600° C. at a heating rate of 20° C./min under air atmosphere. The number average molecular weight (Mn), weight average molecular weight (Mw), and polydispersity index (PDI) were obtained from a gel permeation chromatography (GPC, Agilent 1100 Series). THF was used as a solvent and a refractive index detector was used to obtain the molecular weights of functionalized cellulose acetates.

Example 1

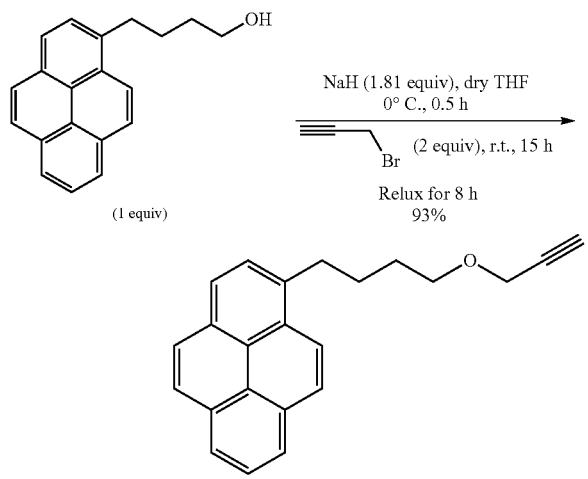

Propargyl pyrenebutyl ether was synthesized according to the following procedure. The reaction was conducted by the procedure described in J. M. Lobez, T. M. Swager, Angew. Chem. Int. Ed. 2010, 49, 95-98. Sodium hydride (NaH, 60 wt % in oil, 0.633 g, 26.39 mmol) was added to a solution of 1-pyrenebutanol (4 g, 14.58 mmol) in dry THF (45 ml) at 0° C. under argon atmosphere. The mixture was stirred at 0° C. for 30 min, and propargyl bromide (80 wt % in toluene, 3.469 g. 29.16 mmol) was added. The solution was stirred at 0° C. in the dark for 30 min and allowed to warm up to room temperature. After stirring for 15 h at room temperature, the reaction was heated to reflux for 8 h. Ethyl acetate (20 ml) and distilled water (20 ml) were added to the solution, and the aqueous phase was extracted twice with 20 ml of ethyl acetate. The combined organic phase was washed with 20 ml of brine and dried over MgSO$_4$. The solvent was removed under vacuum, and the crude product was purified by column chromatography using toluene as an eluent to get the product (4.268 g, 93%). $\delta_H$ (CDCl$_3$) 1.82 (2H, m), 1.96 (2H, m), 2.46 (1H, t, J=2.4 Hz), 3.38 (2H, t, J=7.7 Hz), 3.60 (2H, t, J=6.4 Hz), 4.17 (2H, d, J=2.4 Hz), 7.87~8.32 (9H, m); $\delta_C$ (CDCl$_3$) 28.46, 29.66, 33.33, 58.19, 70.05, 74.31, 80.12, 123.55, 124.75, 124.87, 124.91, 125.12, 125.16, 125.86, 126.64, 127.27, 127.61, 136.81; HRMS (DART) m/z: [M+H]$^+$ calcd for C23H$_{20}$O, 313.1587; found, 313.1571.

Example 2

As shown in FIG. 6, 6-deoxy-6-azido cellulose acetate (CA-N$_3$) was synthesized using cellulose acetate (CA) with an acetyl content of 31.9 wt % (DS$_{Ac}$1.74) as a starting material. CA was soluble in DMSO and DMF, and 51% of the primary hydroxyl groups at the C6 position (estimated from $^{13}$C NMR spectrum) can be utilized for further functionalization while keeping acetate functional groups. Typically azidation is carried out via two step reaction: bromination or tosylation of hydroxyl groups and then azidation using sodium azide. Here, a one-pot azidation reaction was carried out to produce 6-deoxy-6-azido cellulose acetate (CA-N$_3$) with 92% yield by modifying the procedure described in J. Shey, K. M. Holtman, R. Y. Wong, K. S. Gregorski, A. P. Klamczynski, W. J. Orts, G. M. Glenn, S. H. Imam, Carbohydr. Polym. 2006, 65, 529-534. Cellulose acetate (2 g, 8.13 mmol) was premixed with excess sodium azide (NaN$_3$, 5.285 g, 81.3 mmol) in 50 ml of DMF at room temperature for 1 h. In some cases, heating to 100° C. helped to dissolve cellulose acetate in DMF more quickly faster. Triphenylphosphine (PPh$_3$, 4.265 g, 16.26 mmol) was added to the solution at 0° C., and carbon tetrabromide (CBr$_4$, 5.393 g, 16.26 mmol) in 10 ml of DMF was then added dropwise to the solution. The mixture was allowed to warm to room temperature and stirred for 24 h. The degree of substitution of azide was calculated to be 0.41 from elemental analysis. The polymer was precipitated in 700 ml of methanol while stirring. The filtered polymer was further washed with 500 ml of methanol and dried under vacuum at 40° C. for 4 h. CA-N$_3$ was soluble in acetone, THF, DMF, and DMSO. M$_n$: 68 KDa, M$_w$: 123 KDa, PDI: 1.81; Elemental analysis: C, 45.87, H, 4.86, N, 6.94.

Example 3

Pyrene-functionalized cellulose acetate (Py-CA) was synthesized, as shown in FIG. 6. 6-Deoxy-6-azide cellulose acetate (0.1 g, ~0.435 mmol) was dissolved in 10 ml of DMSO, and CuSO$_4$—H$_2$O (12.4 mg, 11 mol %) in 0.5 ml of distilled water and sodium ascorbate (26.4 mg, 29 mol %) in 0.5 ml of distilled water were added to the solution. Propargyl pyrenebutyl ether (0.136 g, 0.435 mmol) in 3 ml of DMSO was added, and the solution was heated to 70° C. while stirring for 24 h under dark. The polymer was substantially completely precipitated in 200 ml of methanol while stirring for about 2 h. The filtered polymer was further washed with 100 ml of H$_2$O and 100 ml of methanol and dried under vacuum at room temperature. The degree of substitution of pyrene selector (DS$_{Py}$) was 0.46 from elemental analysis, and Py-CA was soluble in DMSO and THF. M$_n$: 65 KDa, M$_w$: 138 KDa, PDI: 2.13; Elemental analysis: C, 59.36, H, 5.11, N, 4.82, Cu, 0.63.

Example 4

Benzoate-functionalized CA (Benz-CA) was synthesized according to the method described in Example 3, except that the following reagents were utilized: CuSO$_4$·H$_2$O (6 mol %), sodium ascorbate (14 mol %), and propargyl benzoate (3 equiv). The degree of substitution of benzoate selector (DS$_{Benz}$) was 0.42 from elemental analysis, and Benz-CA was soluble in DMSO and THF. M$_n$: 58 KDa, M$_w$: 166 KDa, PDI: 2.85; Elemental analysis: C50.37, H 4.72, N5.69, Cu 1.35.

Example 5

As shown in FIG. 7, 2,3,4,5,6-Pentafluorophenylacetyl Chloride (F5Ph-Cl) was synthesized by following the method described in E. S. Meadows, S. L. D. Wall. L. J. Barbour, G. W. Gokel, *J. Am. Chem. Soc.* 2001, 123, 3092-3107. To a solution of 2,3,4,5,6-pentafluorophenylacetic acid (2 g, 8.84 mmol) in 100 ml of CH$_2$Cl$_2$ in an ice bath was added dropwise oxalyl chloride (1.122 g, 8.84 mmol). Anhydrous DMF (catalytic amount) was then added. The solution was allowed to warm to room temperature during 2 h, and CH$_2$Cl$_2$ was removed under vacuum.

Example 6

Phenylacetyl chloride (Ph-Cl) was prepared using the procedure described in Example 5.

Example 7

The following example describes the synthesis of 2,3,4,5,6-pentafluorophenyl-acetyl-Functionalized Cellulose Acetate (F5Ph-CA). (FIG. 7) F5Ph-Cl (1.780 g, 7.317 mmol) was added dropwise to a solution of CA (0.9 g, 3.658 mmol) in 20 ml of DMF at 60° C. Triethylamine (0.74 g, 7.317 mmol) was then added as a catalyst, and the mixture was stirred for 4 h at 60° C. The polymer was precipitated in 400 ml of methanol. The filtered product was further washed with 200 ml of methanol and dried under vacuum. The degree of substitution of F5Ph receptor (DS$_{F}$5Ph) was 0.8 from elemental analysis, and F5Ph-CA was soluble in acetone, THF, DMSO, and DMF. M$_n$: 85 KDa, M$_w$: 150 KDa, PDI: 1.77; Elemental analysis: C, 47.46, H, 2.62, N, 0.28, F, 18.98.

Example 8

Phenylacetyl-functionalized cellulose acetate (Ph-CA) was prepared by the same procedure for F5Ph-CA as described in Example 7. The degree of substitution (DS$_{Ph}$) was calculated to be 0.59 from elemental analysis. Ph-CA was soluble in acetone, THF, DMSO, and DMF. M$_n$: 58 KDa, M$_w$: 102 KDa, PDI: 1.76; Elemental analysis: C, 55.97, H, 5.17, N, 0.26.

Example 9

Quartz crystal microbalance (QCM) experiments were performed using Q-sense E1 to test the ability of functionalized cellulose acetates to absorb target analytes by monitoring the frequency change when they were exposed to analyte vapors. The functionalized cellulose acetates were dropcast onto a gold coated AT-cut quartz crystal sensor with 5 MHz fundamental resonance frequency. 20 μg of each material from the solution of 2 mg/ml was deposited on a QCM sensor. Acetone was used as a solvent for F5Ph-CA and Ph-CA, and THF was used for Py-CA and Benz-CA. The films on QCM sensors were tested towards 500 ppm of benzene (0.47% of the saturated vapor) and toluene (1.3% of the saturated vapor) vapors which were generated from a gas generator (FlexStream™ FlexBase Module, KIN-TEK Laboratories, Inc., TX, United States) with dry nitrogen carrier gas. The concentration of vapor was calibrated by measuring mass change of an analyte after purging nitrogen gas through the analyte as a function of time at a fixed flow rate and temperature. The frequency change (the 3$^{rd}$ overtone, f$_3$) of a film on a QCM sensor was measured by three cycles of exposure of a film to an analyte vapor for 1 min. The mass change (Δm) was converted from the frequency change (Δf) using the Sauerbrey equation:

$$\Delta m = -C\frac{1}{n}\Delta f$$

where n is the overtone and C is the mass sensitivity (C=17.7 ngcm$^{-2}$s$^{-1}$).

Example 10

The following example describes the fabrication and use of sensors including two layers: an absorbent material layer (or "preconcentrator" layer) of functionalized cellulose acetates on top of a SWCNT sensing layer. The SWCNT dispersion was prepared by sonicating the solution of SWCNT in THF with 20 μg/ml for 1 h. The SWCNT layer was then prepared by dropcoating 2 μl of the SWCNT solution three times (total 120 ng of SWCNT deposited) onto the screen printed interdigitated array (IDA) microelectrodes (CC1.W1, batch #12C12, BVT technologies, Brno, CZ). The interdigitated array microelectrodes consist of 3 pairs of gold electrodes with 150 μm spacing between electrodes, 150 μm electrode width, and 2000 μm electrode length. The film of functionalized cellulose acetate was then prepared by dropcoating 2 μl of the solution of 1 mg/ml on top of SWCNT layer three times (total 6 μg deposited). The films on the electrodes were dried 12 h at ambient condition before use.

Sensing properties of the devices were measured by monitoring the conductivity change of sensors upon exposure to analytes. The sensors deposited on IDAs were mounted on 2×30 pin edge connector and encased within a custom-built Teflon chamber with an inlet, an outlet, and an internal channel with volume of 7.38 cm$^3$ for gas flow. The analyte vapors of varying concentrations were generated using FlexStream™ FlexBase Module (KIN-TEK Laboratories, Inc., TX, United States) with precise temperature and gas flow rate control. The vapor of varying concentrations was generated by mixing the saturated vapor with dry nitrogen gas and was delivered to the sensor chamber. The concentration of vapor was calibrated by measuring mass change of an analyte after purging nitrogen gas through the analyte as a function of time at a fixed flow rate and temperature. The conductivity measurement was carried out by measuring the current at 0.05V bias voltage using a PalmSense EmStat-MUX equipped with a 16 channel multiplexer (Palm Instruments BV, The Netherlands), and the baseline resistances of sensors were in the range of 5Ω to 15Ω. The sensors were tested by measuring the changes in conductance after several cycles of exposure to the analyte vapor.

The detection limit of a sensor was calculated by extrapolating the linear calibration curve ($-\Delta G/G_o$ vs concentration) when the signal equals three times the noise (J. Li, Y. Lu, Q. Ye, M. Cinke, J. Han, M. Meyyappan, *Nano Lett.* 2003, 3, 929-933). The noise level of a sensor can be calculated from the root-mean square deviation of the data at the baseline. After a fifth-order polynomial fitting of the curve of the normalized conductance change as a function of concentration using Origin 8.0, the variance ($V_{\chi^2}$) was calculated from the residual ($\chi$) between 10 data points at the baseline and curve fitting results by the following equation:

$$V_{\chi^2} = \Sigma(y_i - y)^2$$

where $y_i$ is the measured data point and y is the corresponding value calculated from the curve-fitting equation. The average noise level ($rms_{noise}$) was calculated as follows:

$$rms_{noise} = \sqrt{\frac{V_{\chi^2}}{10}}.$$

The detection limit (LOD at signal-to-noise=3) was calculated as follows:

$$LOD = 3\frac{rms_{noise}}{slope}.$$

Figure 1B:
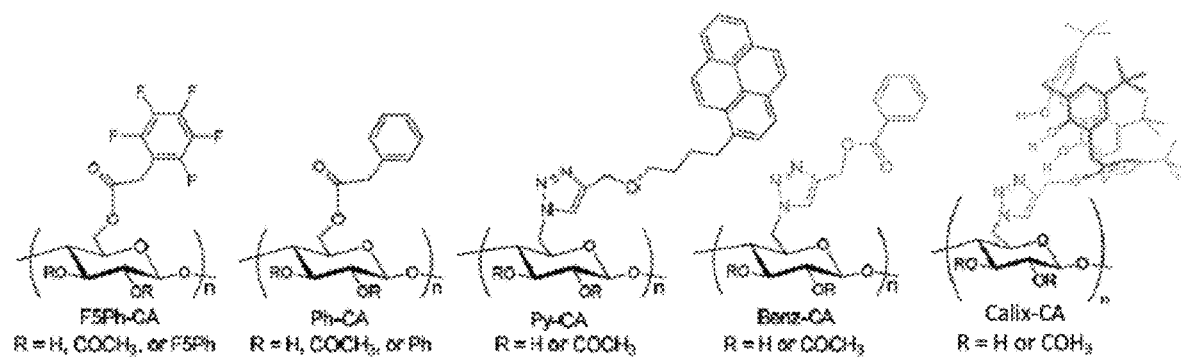
Figure 1C:
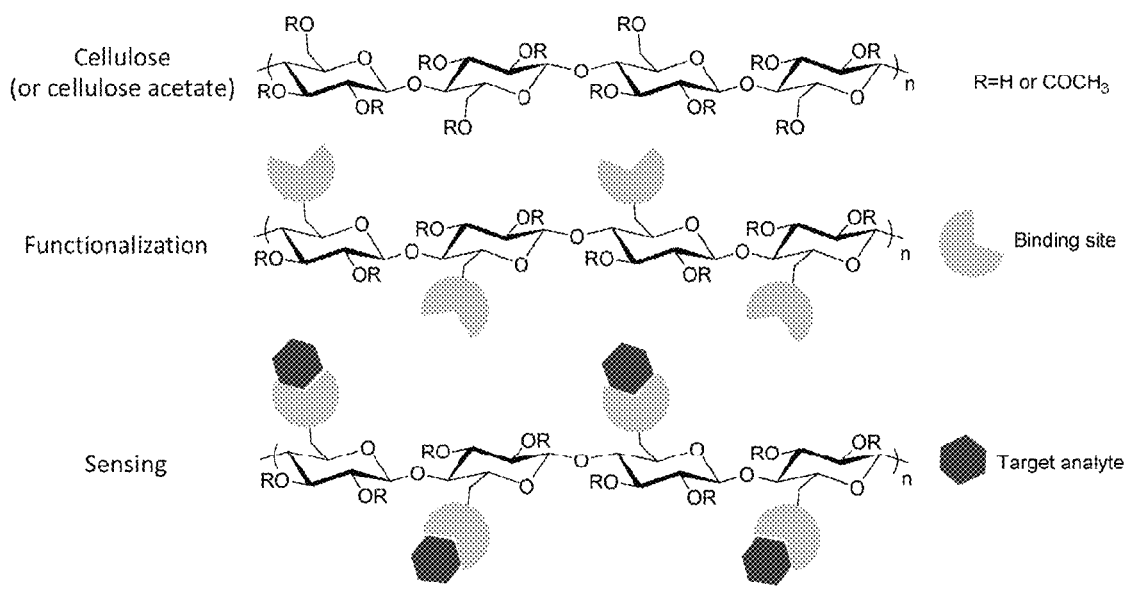
Figure 2A:
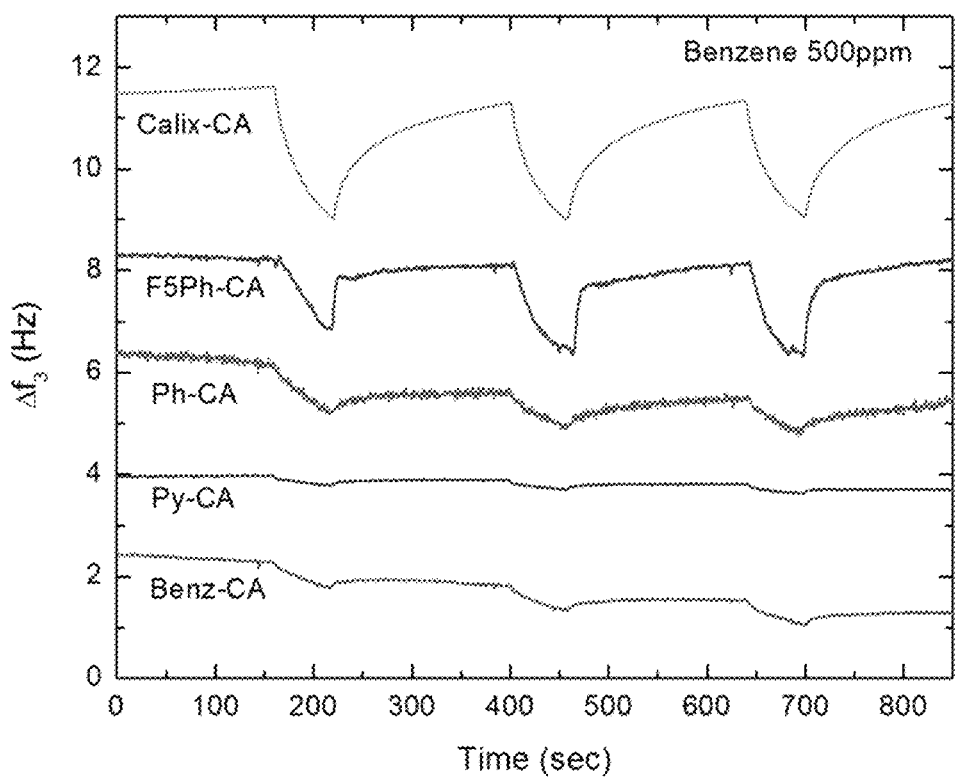
FIGS. 2A-2D shows frequency changes ($\Delta f3$, 3rd overtone) and mass uptakes ($\Delta m$) of the functionalized cellulose acetates of F5Ph-CA, Ph-CA, Py-CA, Benz-CA, and Calix-CA when exposed to 500 ppm of benzene and toluene vapors.
Figure 2B:
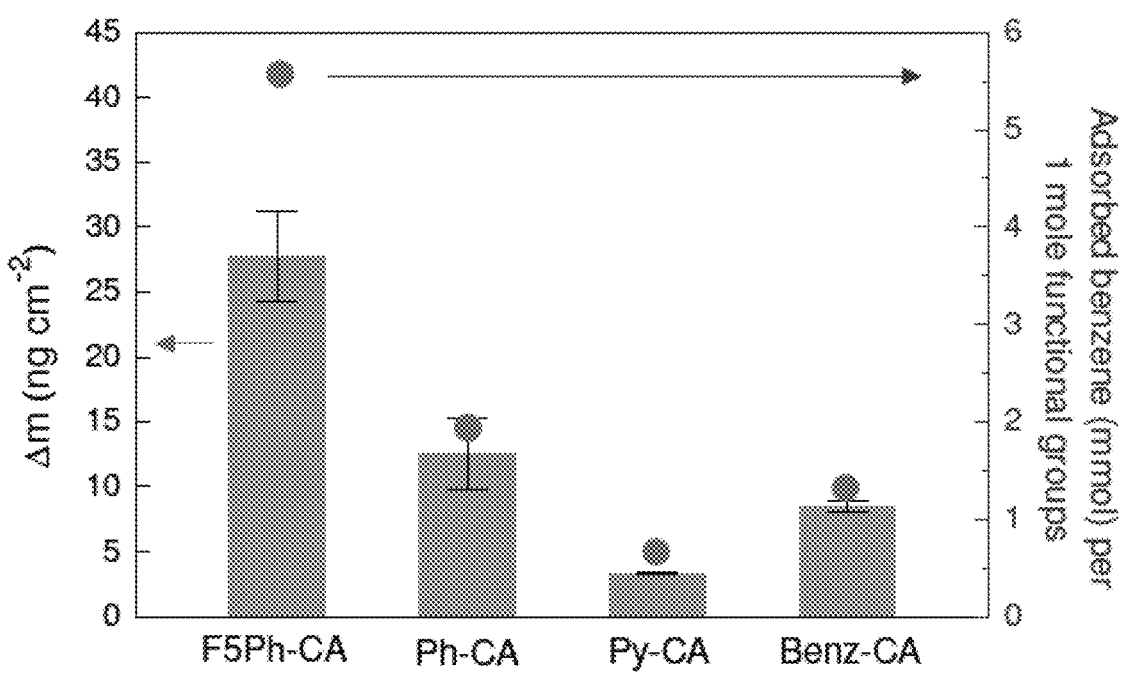
Figure 2C:
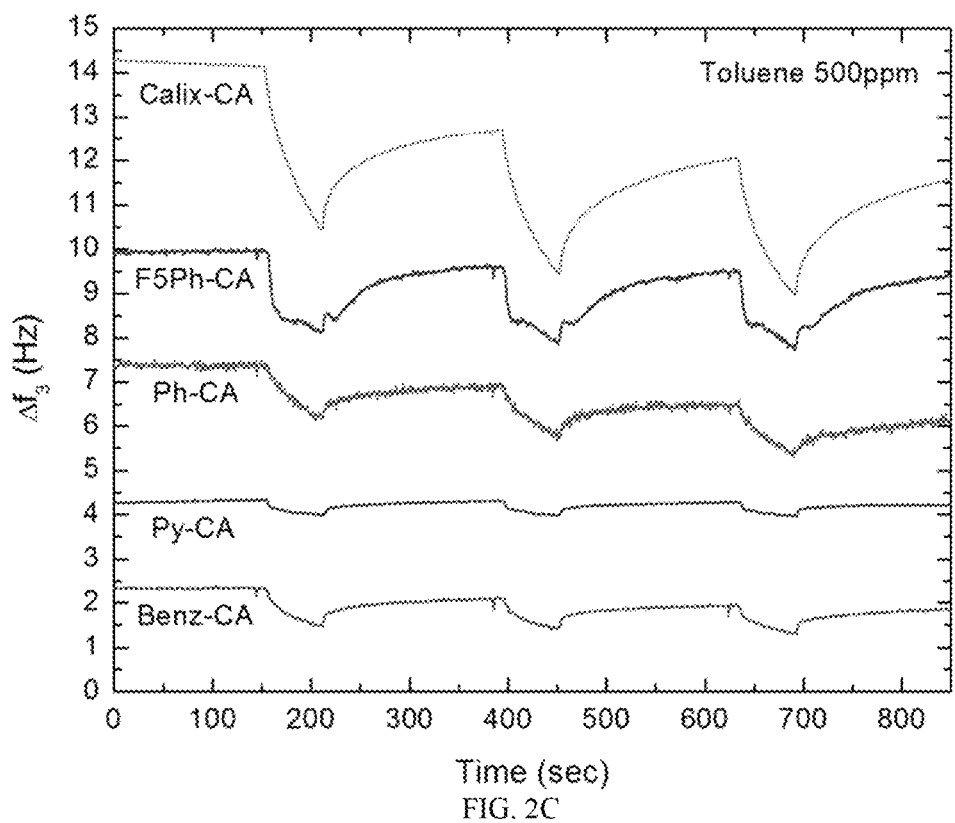
Figure 2D:
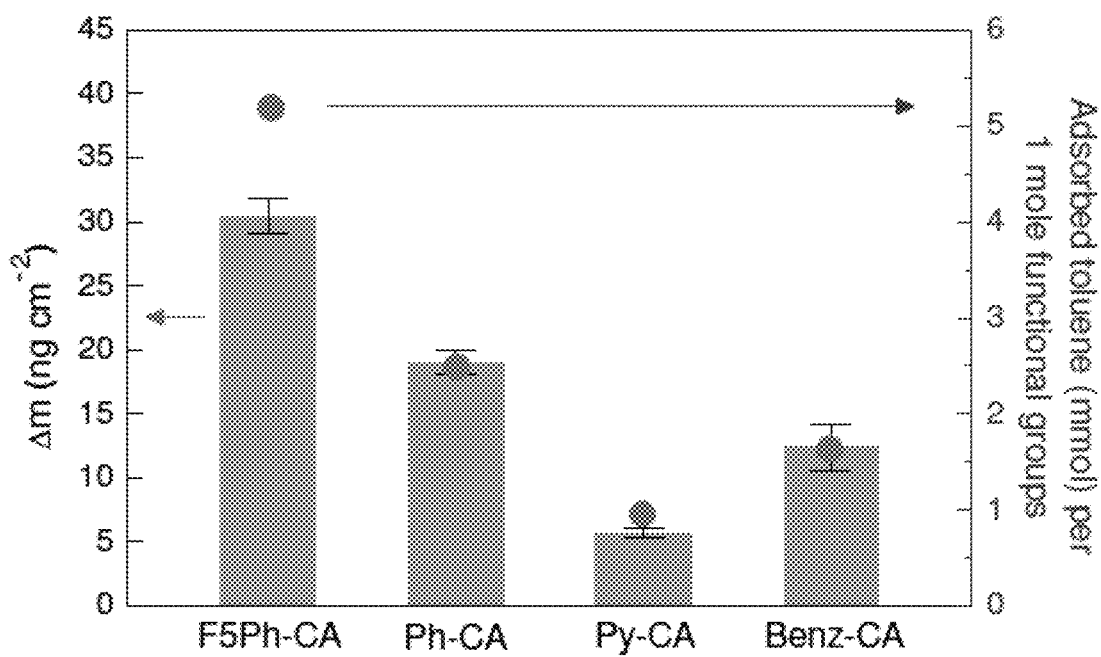
Figure 8:
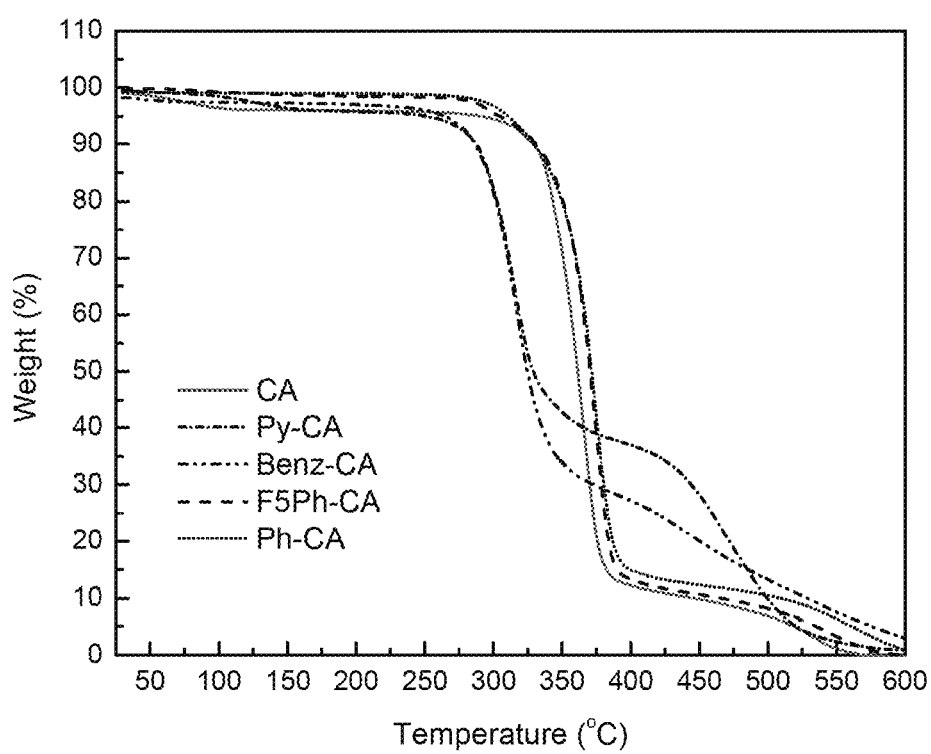
FIG. 8 shows the thermogravimetric analysis (TGA) curves of functionalized cellulose acetates including CA (starting material, DSAc~1.74), Py-CA, Benz-CA, F5Ph-CA, and Ph-CA.

The detection limits of the sensors towards benzene, toluene, m-xylene vapors were 55 ppm, 19 ppm, and 14 ppm, respectively. The simultaneous preconcentrating and sensing steps took only a few seconds, and the response was fully recovered and reproducible. Since the target analyte are aromatic hydrocarbons, CA was functionalized with binding sites having aromatic rings for π-π stacking or electrophilic character for electrostatic interaction. A series of binding sites or receptors, as shown in FIG. 1B, were incorporated into the cellulose acetate backbone via copper (I)-catalyzed azide-alkyne cycloaddition (CuAAC) or esterification reaction. The degrees of substitution (DS) of the benzoate (Benz)-, pyrene (Py)-, 2,3,4,5,6-pentafluorophenylacetyl (F5Ph)-, and phenylacetyl (Ph)-functionalized cellulose acetates were calculated to be 0.42, 0.46, 0.80, and 0.59, respectively, from elemental analysis. FIG. 8 shows the thermogravimetric analysis (TGA) curves of functionalized cellulose acetates including CA (starting material, DSAc~1.74), Py-CA, Benz-CA, F5Ph-CA, and Ph-CA. The functionalized cellulose acetates were thermally stable up to 300° C.

Quartz crystal microbalance (QCM) experiments were performed to test the ability of the functionalized cellulose acetate as a preconcentrator to absorb the target vapor. Mass uptake of the functionalized cellulose acetate film upon exposure to the target vapor was measured by monitoring the frequency change of the film dropcast onto a gold-coated 5 MHz QCM sensor. The films were tested towards 500 ppm of benzene (0.47% of the saturated vapor) and toluene (1.3% of the saturated vapor) generated from a gas generator with dry nitrogen carrier gas. The frequencies (the $3^{rd}$ overtone, $f_3$) of the four functionalized cellulose acetate films including F5Ph-CA, Ph-CA, Py-CA, and Benz-CA decreased upon exposure to both benzene and toluene vapors due to the absorbed vapor molecules on the films. (FIG. 2) The responses were reversible in all cases.

The measured frequency change ($\Delta f$) was converted to the mass density change ($\Delta m$) using Sauerbrey's equation. The absorbed amount (mmol) of an analyte per 1 mole of functional groups was then calculated from $\Delta m$ and degrees of substitution of functional groups and was summarized in FIGS. 2B and 2D. From the QCM results, the F5Ph-CA film showed superior absorbing ability towards benzene and toluene vapors, compared to the other films. The response of the F5Ph-CA to benzene vapor of 500 ppm was more than two times higher than those of the other films. The binding abilities of the four functionalized cellulose acetates to toluene vapor had similar trends to those in response to benzene vapor. Direct comparison of the mass uptakes between the F5Ph-CA (5.576 mmol of absorbed benzene per 1 mole of F5Ph selectors) and Ph-CA (1.937 mmol of absorbed benzene per 1 mole of Ph selectors) films showed that the F5Ph selectors with positive electrostatic potential had stronger interactions with benzene and toluene possessing negative quadrupole moments below and above the aromatic ring. The two products containing triazine rings, Benz-CA and Py-CA, showed less absorption efficiency towards benzene and toluene vapors.

Figure 3:
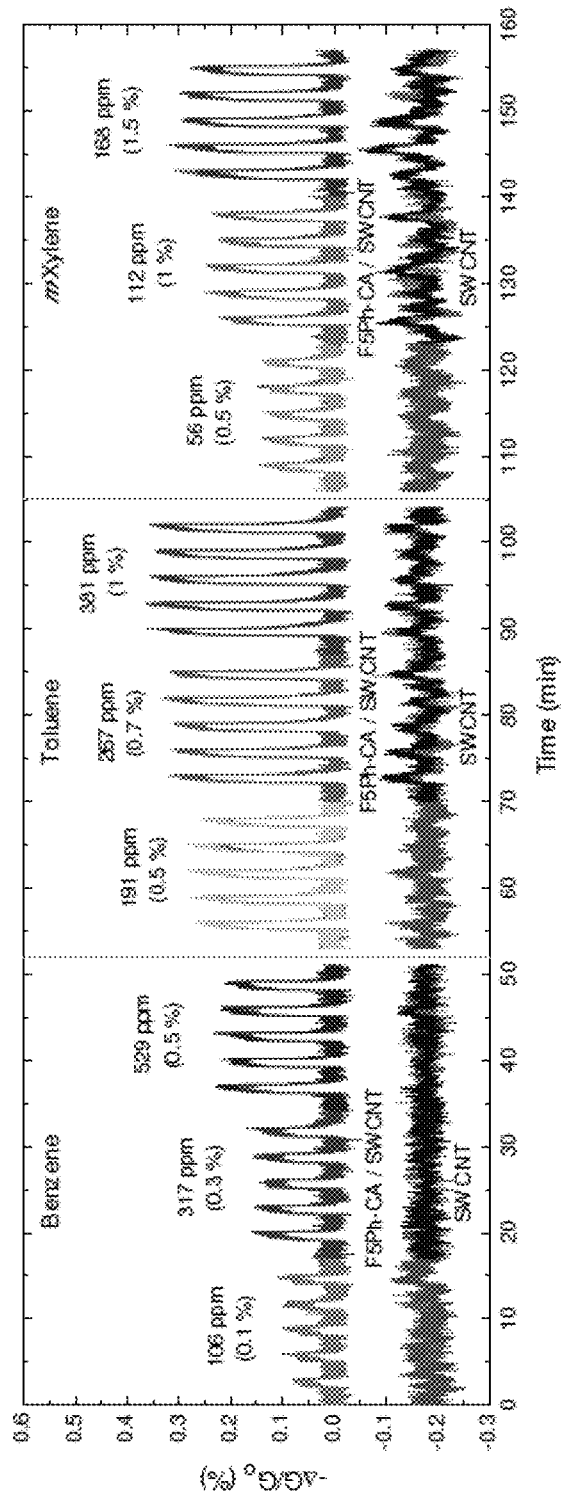
FIG. 3 shows normalized conductance changes [$-\Delta G/Go$ (%)] of the integrated F5Ph-CA preconcentrator/SWCNT system (F5Ph-CA/SWCNT) when exposed to benzene, toluene, and m-xylene vapors of varying concentrations compared to the pristine SWCNT sensor. The responses from a set of duplicate sensors were consistent, as shown by the grey curves representing the sensing response of the second sensor. Simultaneous preconcentrating and sensing took a few seconds.
Figure 9A:
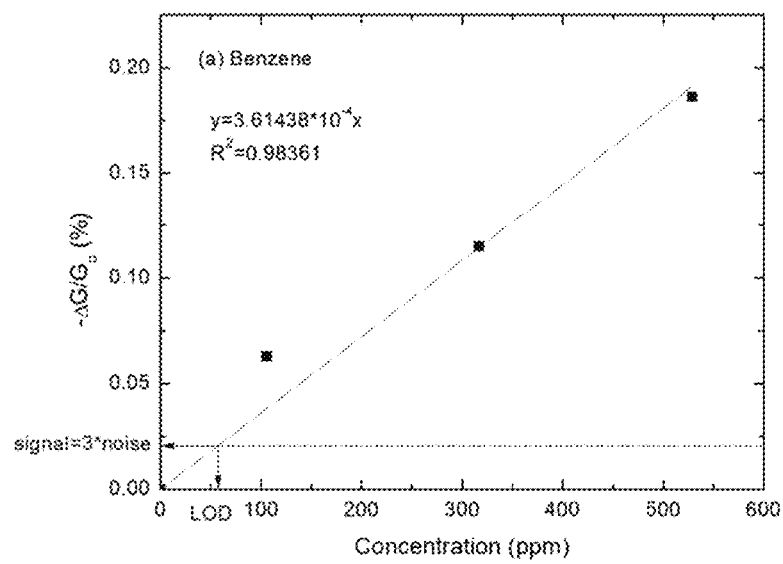
FIGS. 9A-9C shows normalized conductance changes of a F5Ph-CA/SWCNT sensor as a function of concentration of (FIG. 9A) benzene, (FIG. 9B) toluene, and (FIG. 9C) m-xylene vapors showing the limit of detection (LOD) where the signal equals three times the noise.
Figure 9B:
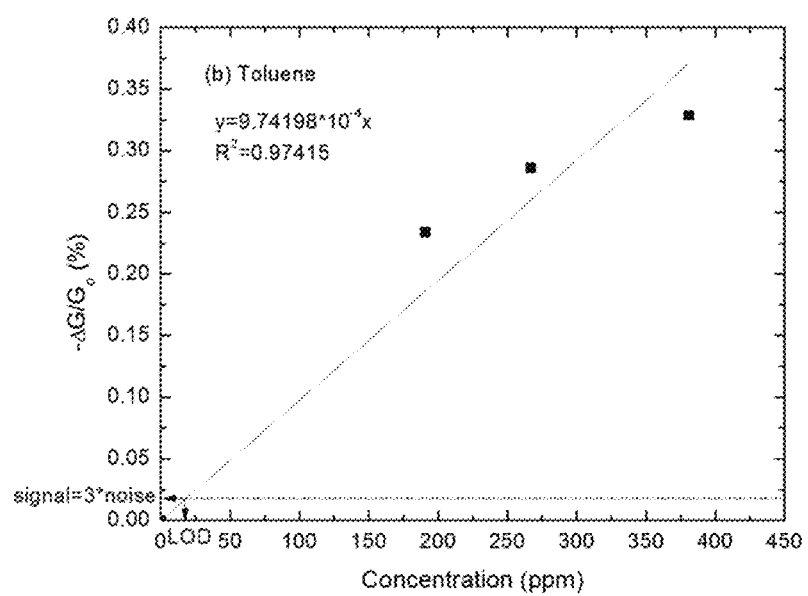
Figure 9C:
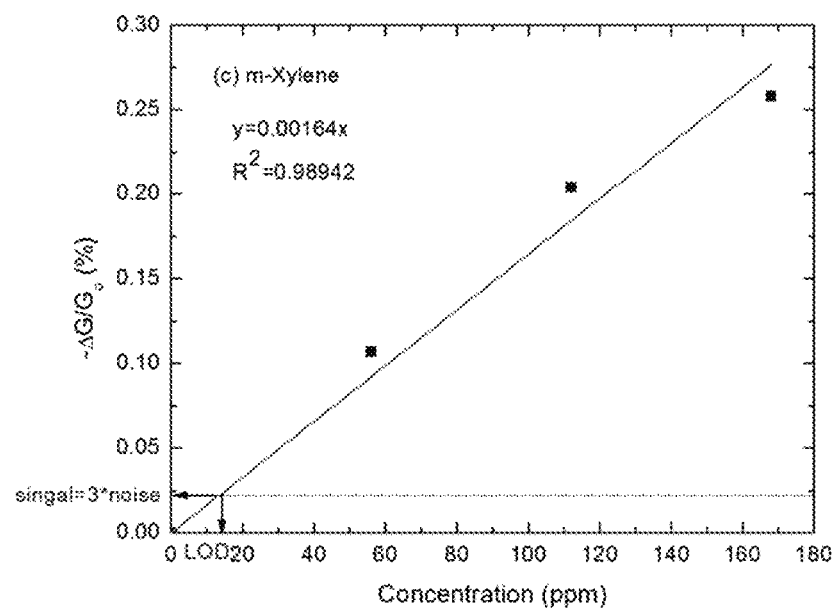

The integrated preconcentrator/sensor system was fabricated by depositing (dropcoating) SWCNT onto interdigitated array microelectrodes followed by dropcoating functionalized cellulose acetate on top of the SWCNT sensing layer. The F5Ph-CA with $DS_{F5Ph}$ of 0.80 was chosen as a preconcentrator from the QCM results shown in FIG. 2. The array consisting of the pristine SWCNT and the integrated F5Ph-CA preconcentrator/SWCNT system (F5Ph-CA/SWCNT) was tested by simultaneously exposing it to an analyte vapor and measuring its current at 0.05V bias voltage. FIG. 3 shows the normalized conductance changes [$-\Delta G/G_o$ (%)] of the pristine SWCNT and F5Ph-CA/SWCNT sensors towards benzene, toluene, and m-xylene vapors of varying concentrations. The normalized conductance changes of both sensors were averaged from two devices of each sensor. As shown in FIG. 3, the conductance of the F5Ph-CA/SWCNT sensor decreased within a few seconds when exposed to benzene, toluene, and m-xylene vapors and the responses of the sensing system were reproducible. The F5Ph-CA/SWCNT sensor was able to detect benzene vapor down to 106 ppm (0.1% of the saturated benzene vapor), as shown in FIG. 3, whereas the pristine SWCNT did not show any response. These results suggest that the F5Ph-CA preconcentrating layer absorbs analytes and delivers the concentrated analytes to the SWCNT sensing layer efficiently. The detection limits of the F5Ph-CA/SWCNT sensor towards benzene, toluene, and in-xylene vapors were calculated to be 55 ppm, 19 ppm, and 14 ppm, respectively, from FIG. 3 when the signal equaled three times the noise level. (FIG. 9) Sensitivity towards toluene and m-xylene vapors exceeded the OSHA PELs of 200 ppm and 100 ppm, respectively.

Figure 4:
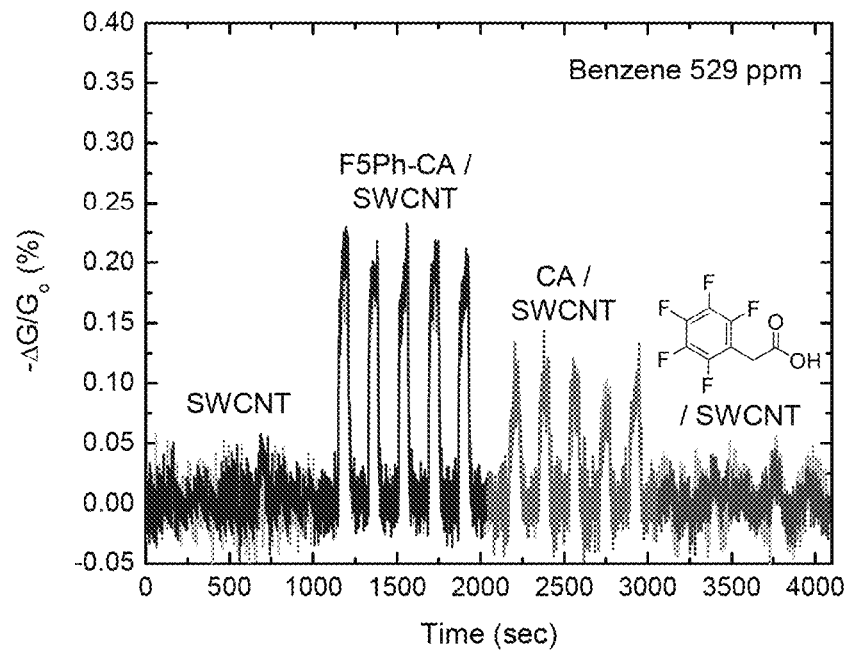
FIG. 4 shows normalized conductance changes of SWCNT, F5Ph-CA/SWCNT, CA/SWCNT, and (2,3,4,5,6-pentafluorophenylacetic acid)/SWCNT systems toward 529 ppm of benzene vapor.

The CA/SWCNT (with $DS_{Ac}$~2.44) and (2,3,4,5,6-pentafluorophenylacetic acid)/SWCNT were also tested toward 529 ppm of benzene vapor to demonstrate the high efficiency of the F5Ph-CA preconcentrator. FIG. 4 shows that the integrated F5Ph-CA/SWCNT sensing system exhibited a superior ability to detect benzene vapor, compared to the other systems. (2,3,4,5,6-Pentafluorophenylacetic acid)/SWCNT did not show any responses to benzene vapor, demonstrating the preconcentrating ability of the functionalized cellulose acetates. The CA/SWCNT sensing system also showed the response to benzene vapor of 529 ppm.

Figure 5:
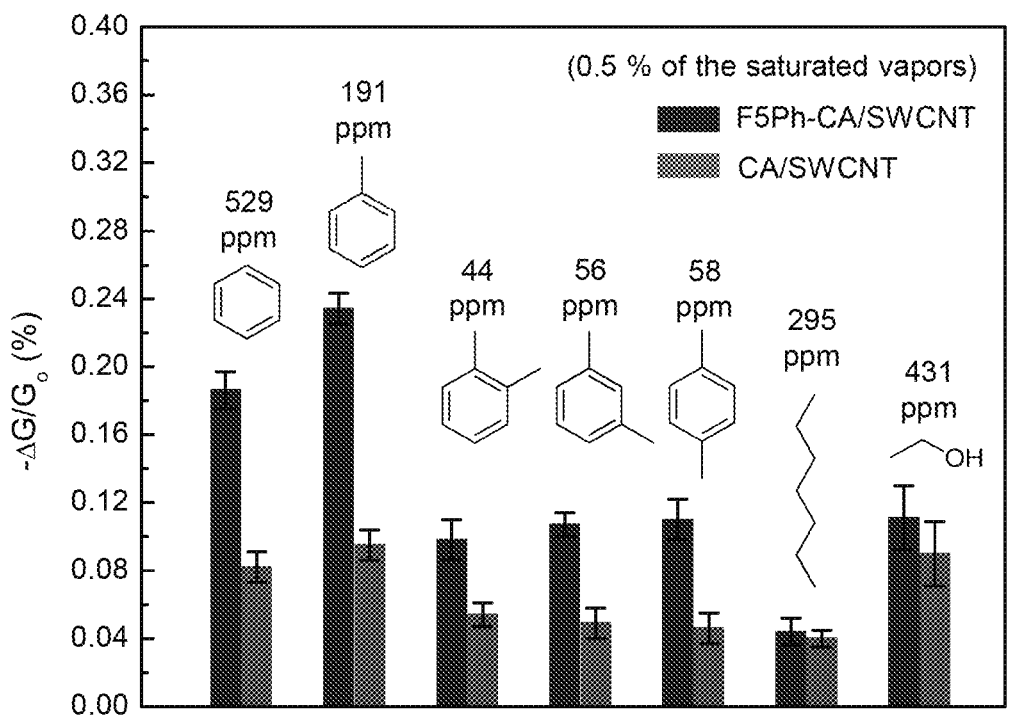
FIG. 5 shows the selectivity chart displaying the responses of the F5Ph-CA/SWCNT and CA/SWCNT systems towards BTX vapors and n-heptane and ethanol as interferents. The concentrations of the analytes were 0.5% of the saturated vapors.

The selectivity of the F5Ph-CA/SWCNT sensor was studied by testing the system in response to benzene, toluene, o-xylene, m-xylene, p-xylene, n-heptane, and ethanol of 0.5% of the saturated vapors. N-heptane and ethanol commonly found in petrochemicals were tested as interferents. FIG. 5 displays the normalized conductance change of the array of the F5Ph-CA/SWCNT and CA/SWCNT sensing systems. The integrated F5Ph-CA/SWCNT system had differential responses to benzene, toluene, and xylenes although it had equivalent responses to the different isomers of xylenes. The responses of the F5Ph-CA/SWCNT to xylenes and ethanol vapors were shown to be similar. However, xylenes and ethanol can be differentiated by having the CA/SWCNT sensor as the part of the array since the responses of the CA/SWCNT to xylenes were 50% of those of the F5Ph-CA/SWCNT while the response of the CA/SWCNT to ethanol was similar to that of the F5Ph-CA/SWCNT. The F5Ph-CA/SWCNT sensor showed the least sensitivity towards n-hexane, which was 24% and 19% of the responses to benzene and toluene vapors, respectively. The selectivity test demonstrates that the F5Ph-CA/SWCNT coupled with the CA/SWCNT sensing system can aid in differentiating benzene, toluene, and xylenes at low ppm concentrations from n-heptane and ethanol interferents.

In summary, a new design for a BTX sensor was demonstrated based on the integrated preconcentrator/SWCNT sensing system where a functionalized cellulose preconcentrating layer was deposited directly on top of the SWCNT sensing layer, allowing preconcentrating and sensing simultaneously within a few seconds. The cellulose acetates functionalized with selectors for target analytes were successfully demonstrated as a preconcentrator. The functionalized cellulose acetate preconcentrating layer selectively absorbed the target analyte and delivered the concentrated analyte to the SWCNT sensing layer, which allowed the system to detect low ppm of BTX vapors. The detection limits towards toluene and xylenes are significantly lower than the OSHA permissible exposure limit. Interdigitated array microelectrodes with smaller gaps represent an approach to produce lower detection limits for BTX gases. The high sensitivity, selectivity, and fast response are significant benefits of the integrated preconcentrator/sensing system, which makes it promising approach for on-site field monitoring applications.

Example 11

Figure 10A:
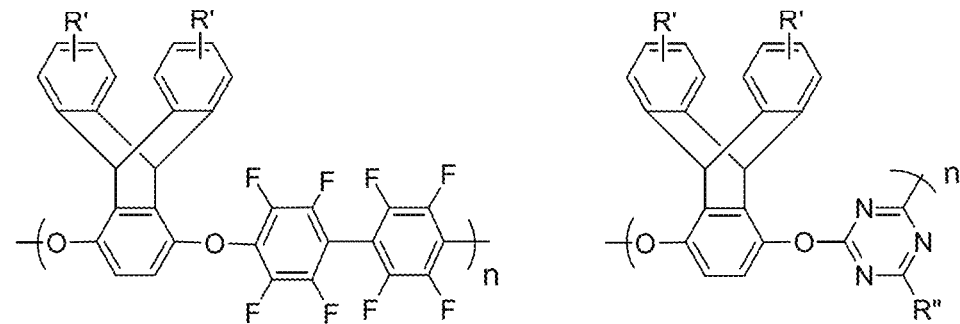
FIGS. 10A-10B shows examples of (FIG. 10A) triptycene-based polymers and (FIG. 10B) pentiptycene-based polymers.
Figure 10A:
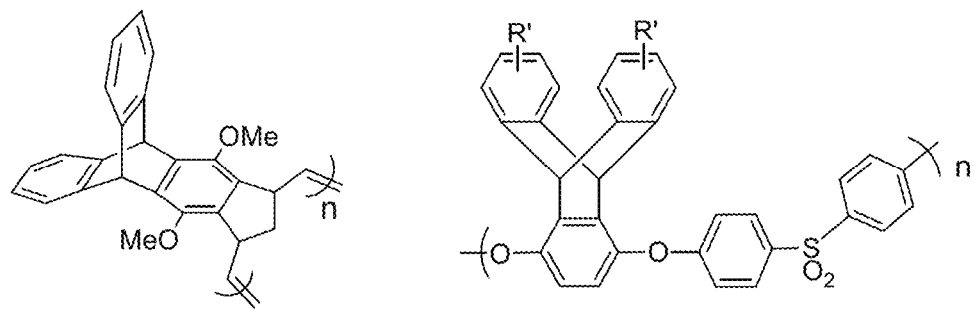
Figure 10A:
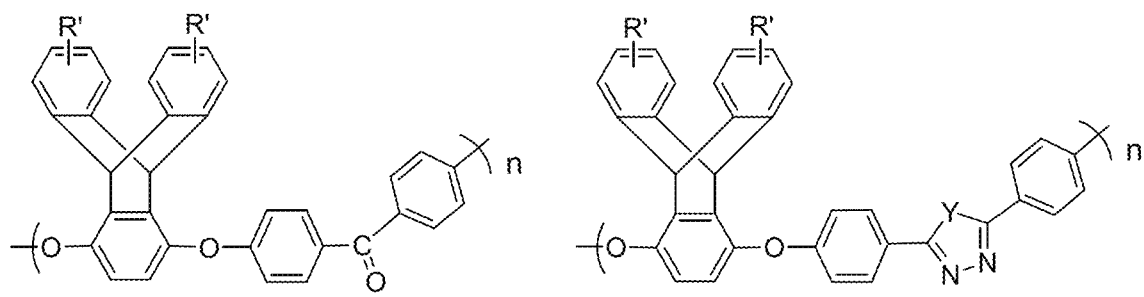
Figure 10B:
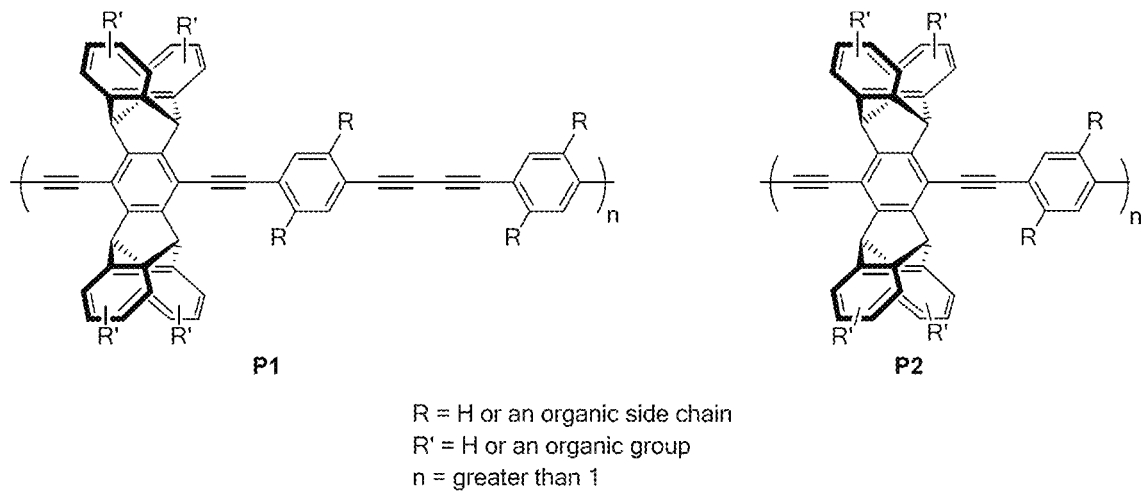
Figure 11:
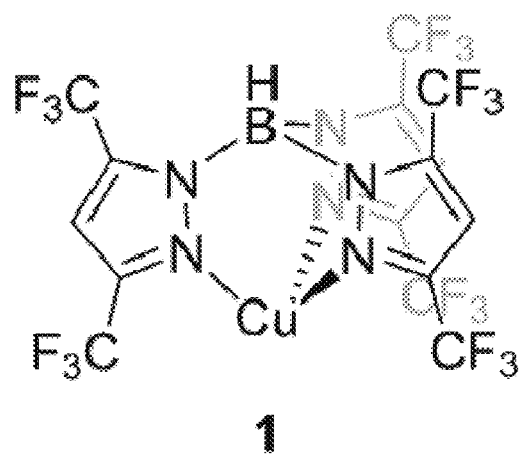
FIG. 11 shows a copper(I) scorpionate complex which can be used as a selector for ethylene.

The following example describes the fabrication and use of sensors including two layers: a polymer layer of pentiptycene polyparaphenlene ethynylene (P2, where $R=OC_{14}H_{29}$) or Poly(p-phenylene butadiynylene) (P1, where $R=OC_{14}H_{29}$), as shown in FIG. 10B, on top of a SWCNT sensing layer containing 3.5 μmol/ml copper(I) scorpionate selector (1). (FIG. 11)

The substrate was prepared by patterning a gold electrode onto a glass slide using thermal evaporation (electrode gap size of 1 mm, gold deposited to a thickness of 100 nm). The SWCNT layer was prepared by sonicating 0.25 mg/ml SWCNT and Cu scorpionate in o-dichlorobenzene/toluene (13:3) for 3 minutes, followed by repeatedly dropcoating 0.5 μl of the solution onto the substrate until a resistance of 1-20 kΩ was achieved. The device was vacuum dried until solvent was completely removed between the addition of each aliquot of solution. Polymer solution (1 μl) was then dropcoated from a solution of 2 mg/ml polymer in THF over each electrode gap that contained SWCNT material.

The sensing properties of the devices were measured by monitoring the conductivity change of sensors upon exposure to analyte. The sensors deposited on the electrodes were mounted on a 2×30 pin edge connector and encased within a custom-built Teflon chamber with an inlet, an outlet, and an internal gas flow channel. 1% Ethylene gas in nitrogen was used as the analyte (AirGas 1.0001%+/−2%). Dry nitrogen gas was used as the carrier gas. Gas mixtures of varying concentrations were generated by mixing the 1% ethylene gas with dry nitrogen gas and were delivered to the sensor chamber using a Sierra Instruments gas mixing system.

The conductivity measurement was carried out by measuring the current at 0.1 V bias voltage using a PalmSense EmStat-MUX equipped with a 16 channel multiplexer (Palm Instruments BV. The Netherlands), and the baseline resistances of sensors were in the range of 1 kΩ to 20 kΩ. The sensors were tested by measuring the changes in conductance after several cycles of exposure to analyte gas.

Figure 12:
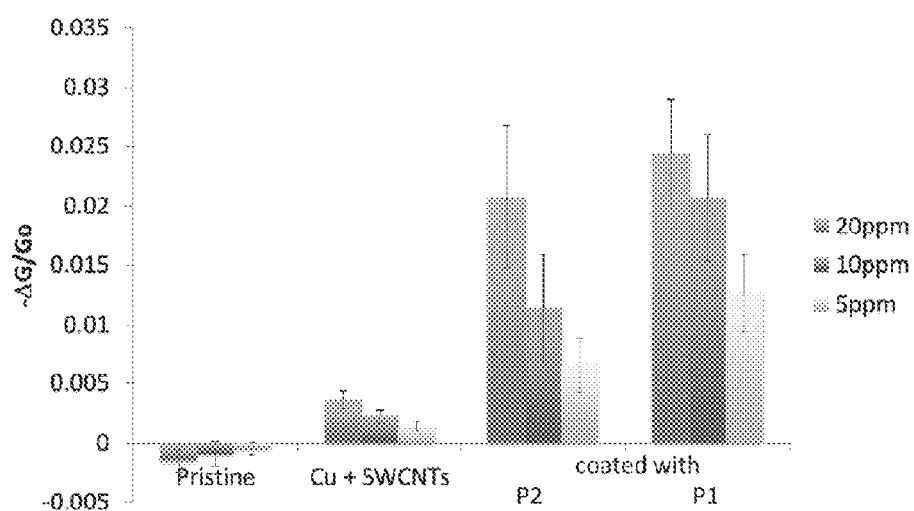
FIG. 12 shows the sensing response of sensors coated with polymers P1 and P2 compared to uncoated sensors to 5, 10, and 20 ppm ethylene.

The sensing response of P2-coated sensors to 20 ppm ethylene was determined to be 2.1% on average. The sensing response of P1-coated sensors to 20 ppm of ethylene was determined to be 2.4% on average. The sensing response of uncoated sensors to 20 ppm of ethylene was 0.35% on average. Measurements were also taken upon exposure to 10 ppm ethylene and 5 ppm ethylene, with the average responses shown in FIG. 12. The relative enhancement of P2-coated sensors over uncoated sensors at 20 ppm ethylene was determined to be 5.8%. The relative enhancement of P1-coated sensors over uncoated sensors at 20 ppm ethylene was determined to be 6.8%.

Example 12

The following example describes the fabrication and use of sensors including two layers: a polymer layer of polymer P3 (as shown in FIG. 13) on top of a SWCNT sensing layer containing a copper(I) scorpionate selector (1).

The substrate was prepared by patterning a gold electrode onto a glass slide using thermal evaporation (electrode gap size of 1 mm, gold deposited to a thickness of 100 nm). The SWCNT layer was prepared by sonicating 0.25 mg/ml SWCNT and Cu scorpionate in o-dichlorobenzene/toluene (13:3) for 3 minutes, followed by repeatedly dropcoating 0.5 μl of the solution onto the substrate until a resistance of 1-20 kΩ was achieved. The device was vacuum dried until solvent was completely removed between the addition of each aliquot of solution. Polymer solution (1 μl) was then drop-coated from a solution of 4 mg/ml polymer in THF over each electrode gap that contained SWCNT material.

Figure 14:
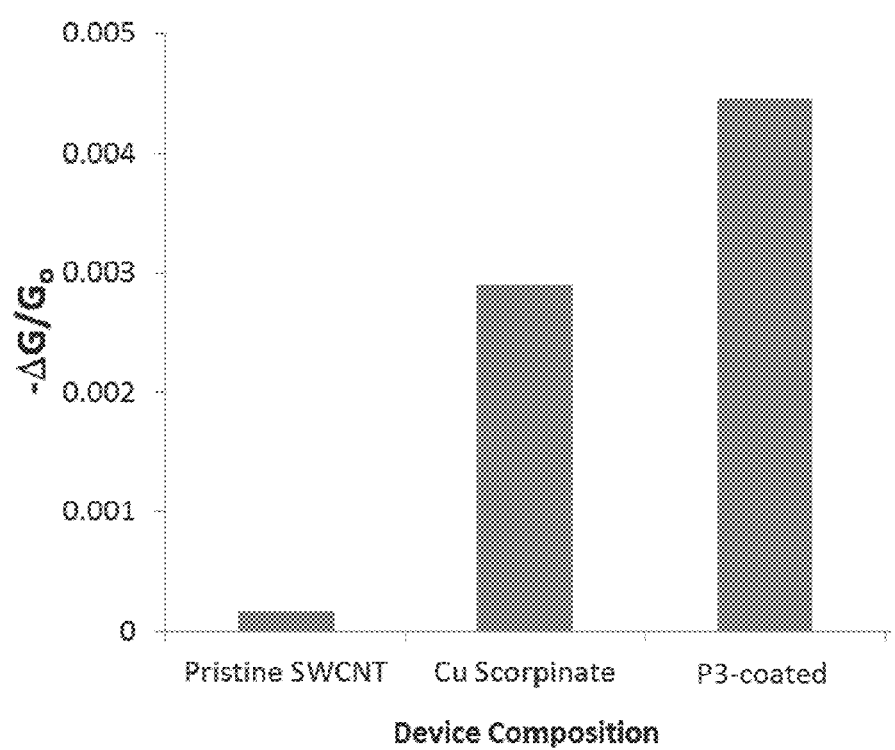
FIG. 14 shows the sensing response of sensors coated with polymer P3 compared to uncoated sensors to 1000 ppm ethylene.

Sensing properties of the devices were measured by monitoring the conductivity change of sensors upon exposure to analyte, using the methods described in Example 11. The sensing response of P3-coated sensors to 1000 ppm ethylene was determined to be 0.44% on average. The sensing response of uncoated sensors to 1000 ppm ethylene was 0.29% on average. Thus, the sensors including the polymer coating exhibited a 1.5% improvement in response to the analyte, relative to uncoated sensors. (FIG. 14)

Example 13

The following example describes the fabrication and use of sensors including two layers: a polymer layer of fluorinated CYTOP polymer (Bellex International Corporation, Japan; structure shown below) on top of a SWCNT sensing layer containing a copper(I) scorpionate selector (1, FIG. 11).
CYTOP:

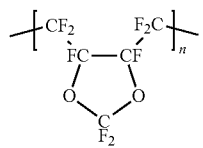

The substrate was prepared by patterning a gold electrode onto a glass slide using thermal evaporation (electrode gap size of 1 mm, gold deposited to a thickness of 100 nm). The SWCNT layer was prepared by sonicating 0.25 mg/ml SWCNT and Cu scorpionate in o-dichlorobenzene/toluene (13:3) for 3 minutes, followed by repeatedly drop-coating 0.5 µl of the solution onto the substrate until a resistance of 1-20 kΩ was achieved. The device was vacuum dried until solvent was completely removed between the addition of each aliquot of solution. A polymer solution (0.2 ml) containing 1:2 CYTOP polymer: CYTOP solvent (Bellex International Corporation, Japan) solution was then spin-coated onto the entire device using a Model WS-400 Spin Processor (Laurell Technologies corporation, USA) at 2000 rpm for 60 seconds. The polymer coating was then dried in a vacuum chamber for 2 minutes.

Figure 15:
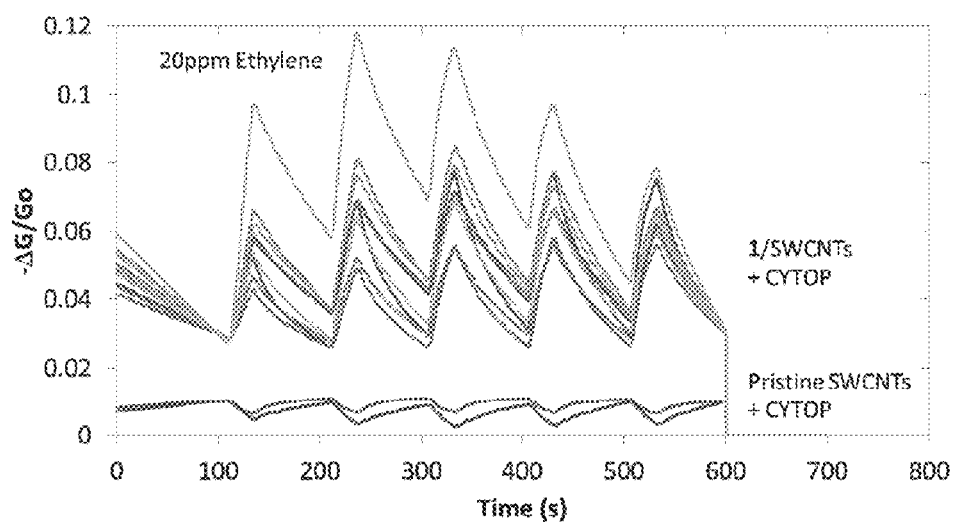
FIG. 15 shows sensing traces from sensors based on 1/SWCNT mixtures and pristine SWCNTs (all coated with CYTOP polymer) in response to 20 ppm ethylene in nitrogen alternating with pure nitrogen.

Sensing properties of the devices were measured by monitoring the conductivity change of sensors upon exposure to analyte, using the methods described in Example 11. The sensing response to 20 ppm ethylene of CYTOP polymer-coated sensors was determined to be 3.1%. The entire device was covered during the application of the polymer using the spin-coating technique so that limited, or substantially no, uncoated reference sensors were available. (FIG. 15)

Example 14

The following example describes the fabrication and use of sensors including two components: a polymeric material (Halocarbon Oil 27) and a SWCNT sensing layer containing copper(I) scorpionate selector (1).

A SWCNT dispersion was prepared by sonicating 0.5 mg SWCNT in 2 ml of a 13:3 mixture of dichlorobenzene: toluene containing copper(I) scorpionate selector 1 for 8 min. Halocarbon oil 27 (5 mg) was mixed with 100 µl of the SWCNT solution by sonication for 30 sec.

Glass slides (VWR Microscope Slides) were cleaned by ultrasonication in acetone for 10 min, rinsing with isopropanol. After drying the glass slides were subjected to UV radiation in a UVO cleaner (Jelight Company Inc.) for 3 min. Using an aluminum mask, layers of chromium (10 nm) and gold (100 nm) were deposited using a custom metal evaporator purchased from Angstrom Engineering leaving a 1 mm gap. The SWCNT sensing layer was then prepared by drop-casting 0.35 µl of the 1/SWCNT/polymer solution between the gold electrodes followed by drying in vacuum until resistances of 5-20 kΩ were achieved.

Sensing properties of the devices were measured by monitoring the conductivity change of sensors upon exposure to ethylene, using the methods described in Example 11. However, ethylene/nitrogen gas mixtures with ethylene concentrations of 20 and 5 ppm were generated using a KIN-TEK gas generating system (KIN-TEK Laboratories, Inc., TX, United States) with precise temperature and gas flow rate control. The varied ethylene concentrations were generated by varying the total flow of 1% ethylene and dry nitrogen gas.

Figure 16:
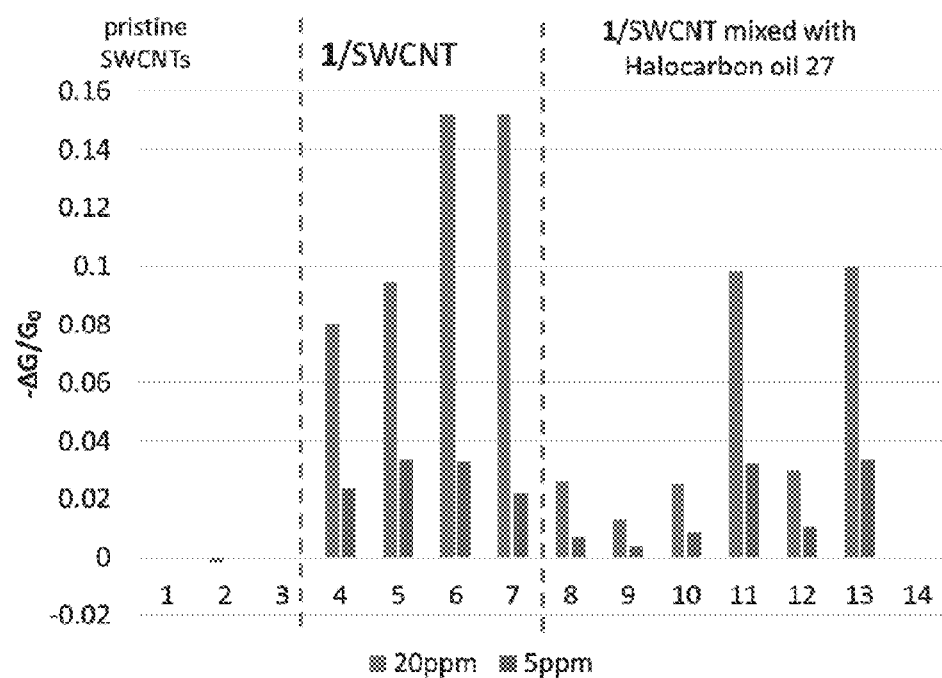
FIG. 16 shows the sensing response of pristine SWCNTs, 1/SWCNTs, and 1/SWCNTs mixed with halocarbon oil 27 to 20 ppm (left columns) and 5 ppm (right columns) ethylene.

The sensors were tested by measuring the changes in conductance after several cycles of exposure to ethylene. The sensing response of the polymer-coated sensors to ppm ethylene and 5 ppm ethylene was determined to be 4.9 and 1.6% on average, respectively, and the sensing response of uncoated sensors was 12.0 and 2.6% on average, respectively. (FIG. 16)

Example 15

The following example describes the fabrication and use of sensors including two layers: a polymeric material layer of different concentrations on top of a SWCNT sensing layer.

A SWCNT dispersion was prepared by sonicating a solution of 0.5 mg SWCNT in 2 ml of a 13:3 mixture of o-dichlorobenzene:toluene containing copper(I) scorpionate selector (1) for 8 min. Glass slides containing layers of chromium (10 nm) and gold (100 nm) were prepared using the method described in Example 14. The SWCNT sensing layer was then prepared by drop-casting 0.35 µl of the SWCNT/polymer suspension between the gold electrodes followed by drying in vacuum until resistances of 5-20 kΩ were achieved. A film of polymer was then prepared by drop-casting 1 µl of a solution of 4 mg Halocarbon oil 27 mixed with 1 ml of THF on top of SWCNT layer once, or in another case, twice (i.e., 2 µl total). The films on the electrodes were dried in vacuum for 30 s before use.

Sensing properties of the devices were measured by monitoring the conductivity change of the sensors upon exposure to ethylene, using the methods described in Example 11. However, ethylene gases of concentrations of 40 ppm, 20 ppm, and 10 ppm were generated using the methods disclosed in Example 14.

Figure 17:
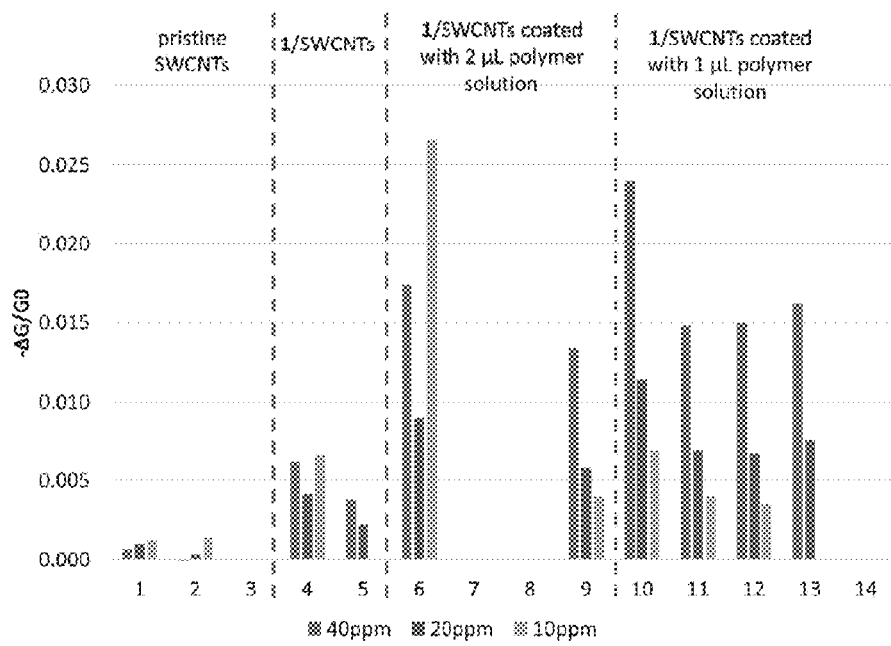
FIG. 17 shows the sensing response of pristine SWCNTs, 1/SWCNTs, and 1/SWCNTs coated with different amounts of halocarbon oil 27 to 40 ppm (left columns), 20 ppm (middle columns), and 10 ppm (right columns) ethylene.

The sensors were tested by measuring the changes in conductance after several cycles of exposure to ethylene. The sensing response of the sensors with and without polymer coating can be seen in FIG. 17.

Example 16

The following example describes the fabrication and use of sensors including two layers: a polymeric material layer of different concentrations on top of a SWCNT sensing layer.

A SWCNT dispersion was prepared by sonicating 0.5 mg SWCNT in 2 ml of a 13:3 solution of dichlorobenzene: toluene containing copper(I) scorpionate selector (1) for 8 min. Glass slides containing layers of chromium (10 nm) and gold (100 mm) were prepared using the method described in Example 14. The SWCNT sensing layer was then prepared by drop-casting 0.35 µl of the SWCNT suspension between the gold electrodes followed by drying in vacuum until resistances of 5-20 kΩ were achieved. A film of polymer was then prepared by drop-casting 1 µl of a solution of 0.5 mg, 4 mg, or 32 mg of Halocarbon oil 27, mixed with 1 ml of THF, on top of SWCNT layer two times. The films on the electrodes were dried in vacuum for 30 s before use.

Sensing properties of the devices were measured by monitoring the conductivity change of sensors upon exposure to ethylene, using the methods described in Example 11. However, ethylene gases of concentrations of 20 ppm, 10 ppm, and 5 ppm were generated the methods disclosed in Example 14.

Figure 18:
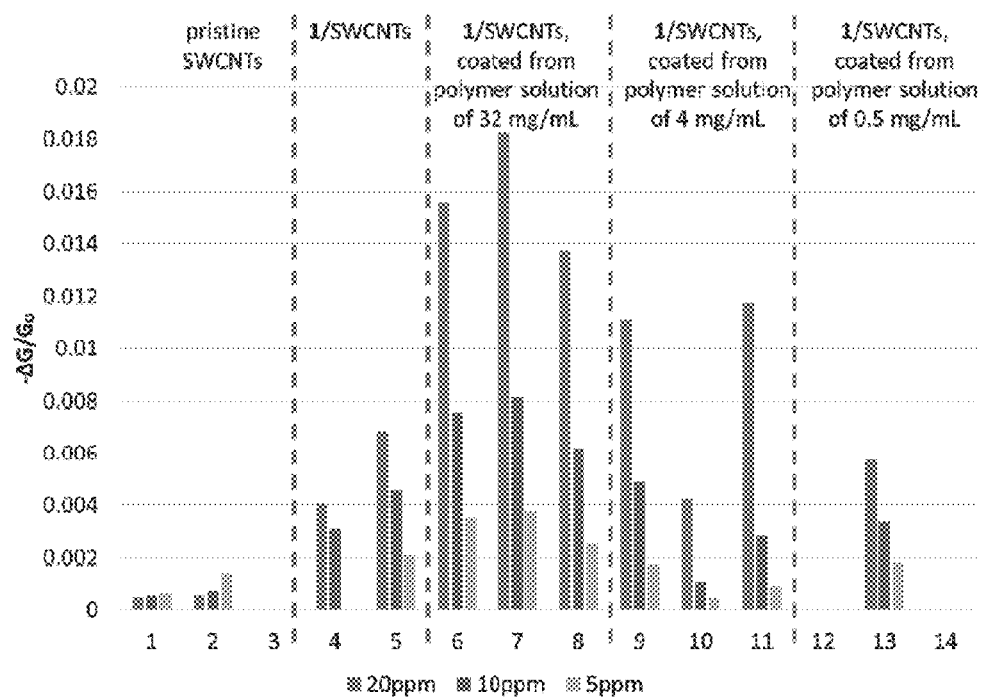
FIG. 18 shows the sensing response of pristine SWCNTs, 1/SWCNTs, and 1/SWCNTs coated with different amounts of halocarbon oil 27 to 20 ppm (left columns), 10 ppm (middle columns), and 5 ppm (right columns) ethylene.

The sensors were tested by measuring the changes in conductance after several cycles of exposure to ethylene. The sensing response of the sensors with and without polymer coating can be seen in FIG. 18.

Example 17

The following example describes the fabrication and use of sensors including two layers: a polymeric material layer of different concentrations on top of a SWCNT sensing layer.

A SWCNT dispersion was prepared by sonicating a solution of 0.5 mg SWCNT in 2 ml of a 13:3 mixture of o-dichlorobenzene:toluene containing copper(I) scorpionate selector (1) for 8 min. Glass slides containing layers of chromium (10 nm) and gold (100 urn) were prepared using the method described in Example 14. The SWCNT sensing layer was then prepared by drop-casting 0.35 μl of the SWCNT solution in between the gold electrodes followed by drying in vacuum until resistances of 5-20 kΩ were achieved. A film of polymer was then prepared by drop-casting two times 1 μl of a solution of 32 mg, 50 mg, or 100 mg Halocarbon oil 27, mixed in 1 ml THF, on top of SWCNT layer. The films on the electrodes were dried in vacuum for 30 s before use.

Sensing properties of the devices were measured by monitoring the conductivity change of sensors upon exposure to ethylene, using the methods described in Example 11. However, ethylene gases of concentrations of 20 ppm, 10 ppm, and 5 ppm were generated using the methods disclosed in Example 14.

Figure 19:
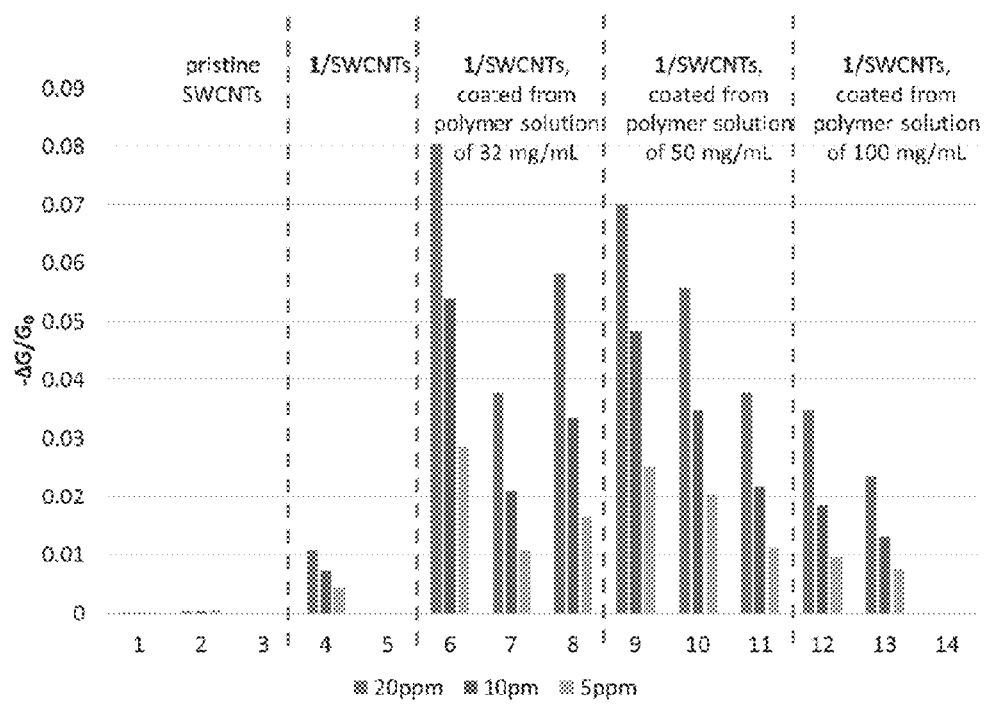
FIG. 19 shows the sensing response of pristine SWCNTs, 1/SWCNTs, and 1/SWCNTs coated with different amounts of halocarbon oil 27 to 20 ppm (left columns), 10 ppm (middle columns), and 5 ppm (right columns) ethylene.

The sensors were tested by measuring the changes in conductance after several cycles of exposure to ethylene. The sensing response of the sensors with and without polymer coating can be seen in FIG. 19.

Example 18

The following example describes the fabrication and use of sensors including two layers: a polymeric material layer of different concentrations on top of a SWCNT sensing layer.

A SWCNT dispersion was prepared by sonicating a solution of 0.5 mg SWCNT in 2 ml of a 13:3 mixture of o-dichlorobenzene:toluene containing copper(I) scorpionate selector (1) for 8 min. Glass slides containing layers of chromium (10 nm) and gold (100 nm) were prepared using the method described in Example 14. The SWCNT sensing layer was then prepared by drop-casting 0.35 μl of the SWCNT solution in between the gold electrodes followed by drying in vacuum until resistances of 5-20 kΩ were achieved. A film of polymer was then prepared by drop-casting, either once or twice (i.e., 2 μl total), 1 μl of a solution of 4 mg Halocarbon oil 700 mixed with 1 ml THF on top of SWCNT layer. The films on the electrodes were dried in vacuum for 30 s before use.

Sensing properties of the devices were measured by monitoring the conductivity change of sensors upon exposure to ethylene, using the methods described in Example 11. However, ethylene gases of concentrations of 40 ppm, 20 ppm, and 10 ppm were generated using the methods disclosed in Example 14.

Figure 20:
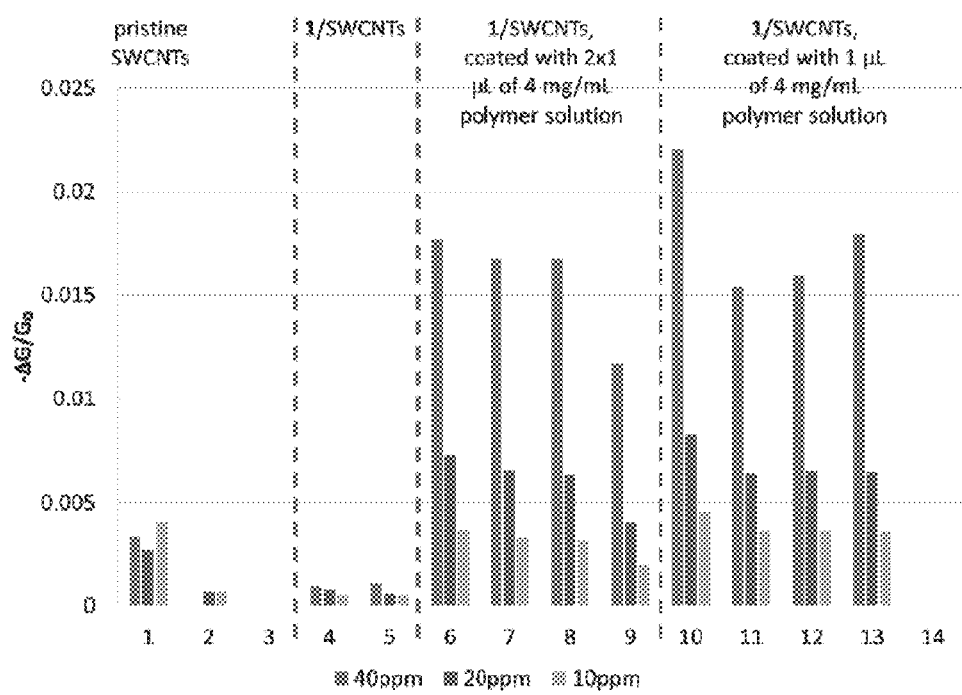
FIG. 20 shows the sensing response of pristine SWCNTs, 1/SWCNTs, and 1/SWCNTs coated with different amounts of halocarbon oil 700 to 40 ppm (left columns), 20 ppm (middle columns), and 10 ppm (right columns) ethylene.
Figure 21:
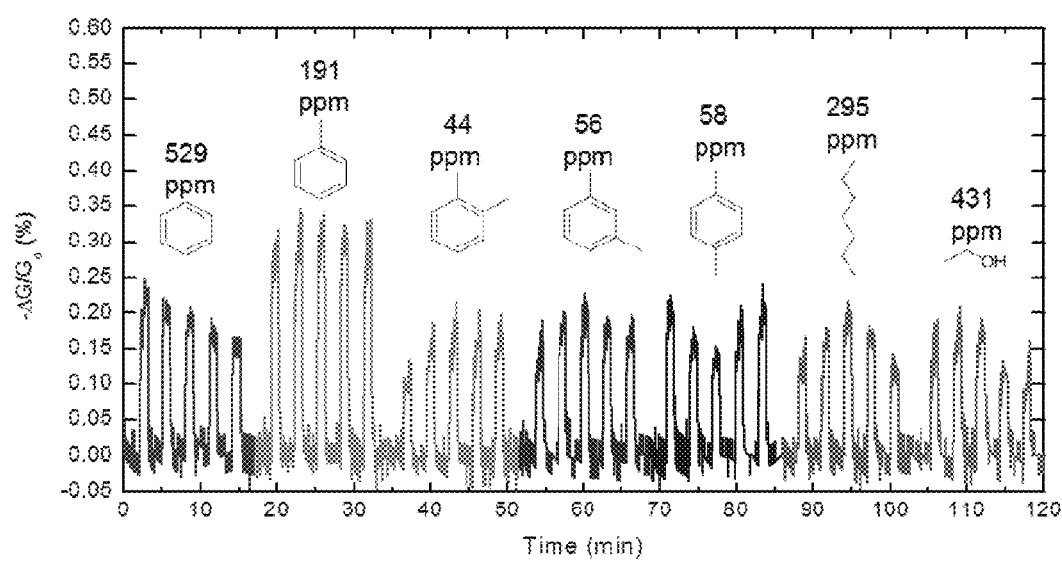
FIG. 21 shows normalized conductance changes [$-\Delta G/Go$ (%)] of the Calix-CA preconcentrator when exposed to vapors of varying concentrations.

The sensors were tested by measuring the changes in conductance after several cycles of exposure to ethylene. The sensing response of the sensors with and without polymer coating can be seen in FIG. 20.

What is claimed:

1. A device for determining an analyte, comprising:
   a sensor material layer comprising a conductive material comprising carbon nanotubes; and
   an absorbent material layer disposed on the sensor material layer,
   wherein the absorbent material interacts with an analyte, if present, in a manner bringing the analyte into proximity with the sensor material layer to produce a determinable signal from the device,
   wherein the absorbent material layer comprises a functionalized cellulose-based polymer and/or an iptycene-based polymer,
   wherein the absorbent material layer acts as a preconcentrator for the analyte, and
   wherein the absorbent material layer optionally comprises an ionic liquid,
   wherein the cellulose-based polymer comprises the structure,

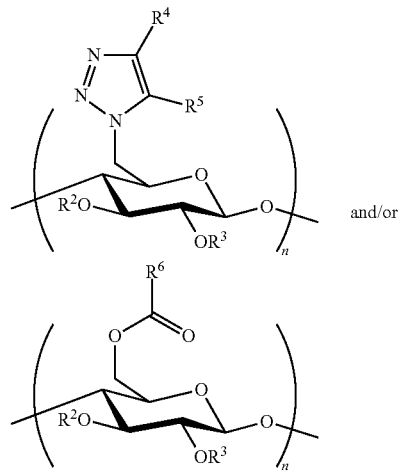

and/or wherein $R^2$ and $R^3$ can be the same or different and are hydrogen, alkyl, aryl, a carbonyl group, any of which is optionally substituted,
   wherein $R^4$ and $R^5$ can be the same or different and are hydrogen, alkyl, alkenyl, aryl, heteroalkyl, heteroalkenyl, heteroaryl, or carbonyl group, any of which is optionally substituted,
   wherein $R^6$ is alkyl, alkenyl, aryl, heteroalkyl, heteroalkenyl, or heteroaryl, any of which is optionally substituted, and
   wherein n is greater than 1.

2. A device as in claim 1, wherein the device lacks a piezoelectric material.

3. A device as in claim 1, wherein the absorbent material layer comprises a polymer material and a plurality of binding sites.

4. A device as in claim 1, wherein the ionic liquid comprises an imidazolium ion.

5. A device as in claim 4, wherein the imidazolium ion is selected from a group consisting of 1-Butyl-3-methylimidazolium, 1-Ethyl-3-methylimidazolium, and 1-Hexyl-3-methylimidazolium.

6. A device as in claim 1, wherein the ionic liquid comprises a cation selected from a group consisting of tetrafluoroborate, hexafluorophosphate, and bis(trifluoromethanesulfone)imide.

7. A device as in claim 1, wherein the cellulose-based polymer is cellulose acetate, cellulose diacetate, or cellulose triacetate, any of which is optionally substituted.

8. A device as in claim 1, wherein the cellulose-based polymer is cellulose substituted with at least one functional group comprising an aromatic moiety.

9. A device as in claim 3, wherein the plurality of binding sites comprises an aromatic moiety, a calixarene, a hydrogen bond donor, or a hydrogen bond acceptor.

10. A device as in claim 9, wherein the aromatic moiety is a phenyl group, optionally substituted.

11. A device as in claim 9, wherein the aromatic moiety is a polycyclic aromatic hydrocarbon, optionally substituted.

12. A device as in claim 1, wherein $R^4$, $R^5$, and/or $R^6$ are selected such that the cellulose-based polymer comprises a function group selected from the group consisting of,

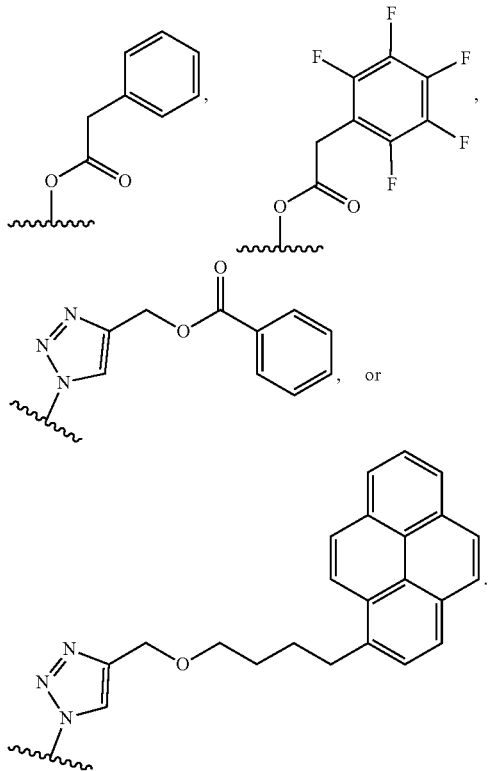

13. A device as in claim 1, wherein $R^2$ and $R^3$ can be the same or different and are hydrogen, —COCH$^3$, or —F$^5$Ph.

14. A device as in claim 13, wherein $R^2$ and $R^3$ are the same.

15. A device as in claim 13, wherein $R^2$ and $R^3$ are different.

16. A device as in claim 1, wherein the carbon nanotubes are single-wall carbon nanotubes.

17. A device as in claim 1, wherein the carbon nanotubes are multi-wall carbon nanotubes.

18. A device as in claim 1, wherein the sensor material layer and/or absorbent material layer further comprises a species capable of interacting with the analyte.

19. A device as in claim 1, wherein the sensor material layer and/or absorbent material layer further comprises a metal-containing species.

20. A device for determining an analyte, comprising:
a first electrode and a second electrode;
a sensor material in electrochemical communication with the first and the second electrodes, wherein resistance to current flow between the first and second electrode is affected by the sensor material; and
an absorbent material in contact with and disposed on the sensor material,
wherein the absorbent material layer comprises a functionalized cellulose-based polymer and/or an iptycene-based polymer,
wherein the absorbent material optionally comprises an ionic liquid;
wherein the absorbent material acts as a preconcentrator for the analyte;
wherein the sensor material comprises a carbon nanotubes, and
wherein the absorbent material interacts with the analyte, if present, in a manner bringing the analyte into proximity with the sensor material such that resistance to current flow between the first and second electrodes is affected, thereby generating a signal in the device by which the analyte is determined,
wherein the cellulose-based polymer comprises the structure,

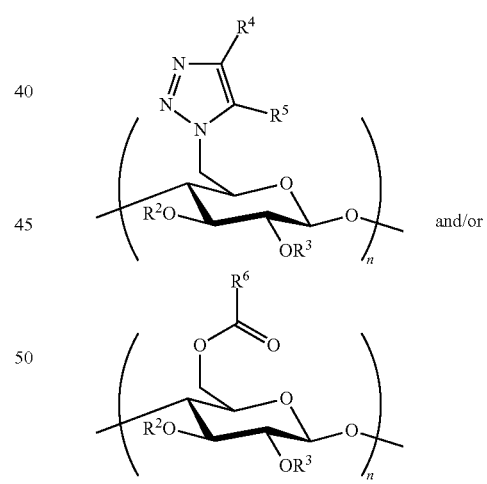

wherein $R^2$ and $R^3$ can be the same or different and are hydrogen, alkyl, aryl, a carbonyl group, any of which is optionally substituted,
wherein $R^4$ and $R^5$ can be the same or different and are hydrogen, alkyl, alkenyl, aryl, heteroalkyl, heteroalkenyl, heteroaryl, or carbonyl group, any of which is optionally substituted,
wherein $R^6$ is alkyl, alkenyl, aryl, heteroalkyl, heteroalkenyl, or heteroaryl, any of which is optionally substituted, and
wherein n is greater than 1.

21. A device as in claim 20, wherein the device lacks a piezoelectric material.

\* \* \* \* \*